(12) United States Patent
Nevo

(10) Patent No.: US 12,318,076 B2
(45) Date of Patent: Jun. 3, 2025

(54) CURVED NEEDLE CORE BIOPSY SYSTEM

(71) Applicant: Erez Nevo, Baltimore, MD (US)

(72) Inventor: Erez Nevo, Baltimore, MD (US)

( * ) Notice: Subject to any disclaimer, the term of this patent is extended or adjusted under 35 U.S.C. 154(b) by 1058 days.

(21) Appl. No.: 17/292,786

(22) PCT Filed: Nov. 12, 2019

(86) PCT No.: PCT/IB2019/059714
§ 371 (c)(1),
(2) Date: May 11, 2021

(87) PCT Pub. No.: WO2020/100038
PCT Pub. Date: May 22, 2020

(65) Prior Publication Data
US 2021/0393243 A1 Dec. 23, 2021

Related U.S. Application Data

(60) Provisional application No. 62/758,745, filed on Nov. 12, 2018.

(51) Int. Cl.
*A61B 10/02* (2006.01)
*A61B 34/20* (2016.01)

(52) U.S. Cl.
CPC .......... *A61B 10/0266* (2013.01); *A61B 34/20* (2016.02); *A61B 2010/0208* (2013.01); *A61B 2034/2046* (2016.02)

(58) Field of Classification Search
CPC ................ A61B 10/0266; A61B 34/20; A61B 2010/0208
See application file for complete search history.

(56) References Cited

U.S. PATENT DOCUMENTS

| | | | |
|---|---|---|---|
| 3,342,175 A | 9/1967 | Bulloch | |
| 4,940,061 A | 7/1990 | Terwilliger et al. | |
| 5,334,185 A | 8/1994 | Giesy et al. | |
| 8,388,550 B2 | 3/2013 | Koehler et al. | |
| 2004/0133124 A1 | 7/2004 | Bates et al. | |
| 2005/0165328 A1* | 7/2005 | Heske ................ | A61B 10/0275 600/568 |
| 2011/0295199 A1* | 12/2011 | Popovic ............. | A61B 17/3421 604/95.01 |
| 2012/0220894 A1* | 8/2012 | Melsheimer ....... | A61B 10/0275 600/567 |

FOREIGN PATENT DOCUMENTS

| WO | WO9713542 | 4/1997 |
|---|---|---|
| WO | WO2009144653 | 12/2009 |

* cited by examiner

*Primary Examiner* — Christian Jang
(74) *Attorney, Agent, or Firm* — AlphaPatent Associates Ltd.; Daniel J. Swirsky

(57) ABSTRACT

A core biopsy system includes a core biopsy needle device having a curvable core biopsy needle which is positionable within and movable with respect to a coaxial needle guide. Systems and methods for obtaining biopsy samples from multiple locations with a single insertion of a needle of the biopsy needle device include controlling rotation and displacement of the core biopsy needle. Additional features and methods of the invention include tracking and planning of the obtaining of biopsy samples.

11 Claims, 20 Drawing Sheets

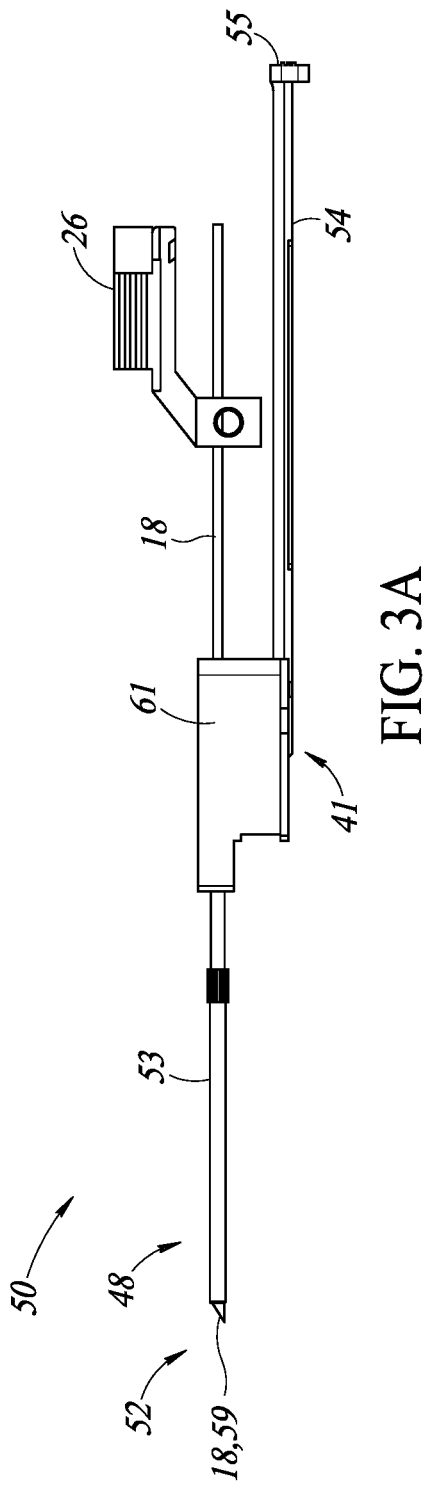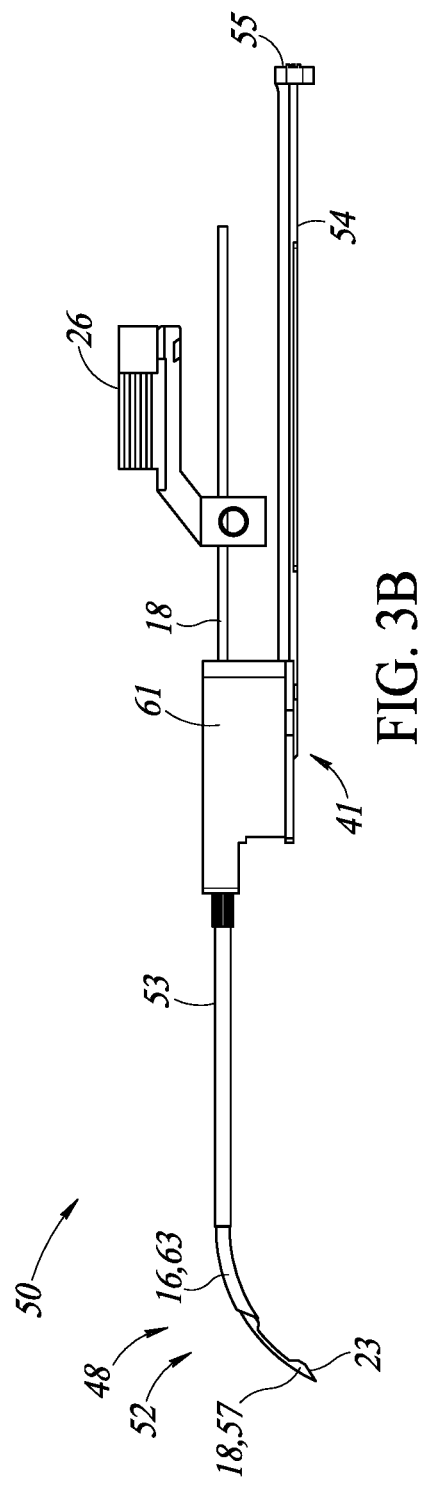

CURVED NEEDLE CORE BIOPSY SYSTEM

CROSS-REFERENCE TO RELATED APPLICATIONS

The present application claims the benefit of U.S. Provisional Patent Application No. 62/758,745, filed Nov. 12, 2018.

FIELD

The invention relates to a system and method for needle core biopsy which provides for multiple biopsy sample extraction.

BACKGROUND

Biopsy devices are commonly used to acquire tissue from the body, typically from pathologies like tumors, and are fundamental in the diagnosis of a disease and the assessment of its prognosis.

Core biopsy needles are typically built of two components: a stylet—a thin, elongated, round bar with a notch for the tissue sample; and a cutting cannula—a thin-walled tube surrounding the stylet which cuts the tissue sample from the surrounding tissue. The needles are typically integrated with a handle that includes a firing mechanism to facilitate the tissue sample cutting.

In most clinical applications, more than one biopsy sample is needed. When several biopsy samples are acquired, the common clinical practice is to remove the needle from the body after each tissue acquisition and to remove the sample from the notch into a small tray—either kept in room temperature or cooled by ice. Following the acquisition of all samples, the samples can be stabilized by freezing or by chemical preservation (e.g. with formalin). The time between the sample acquisition and the sample's preservation can be highly variable, from a few minutes up to an hour. This may result in substantial changes in the biomolecular profile of the tissue.

Thus, there is a need for a system and a method that will provide multiple samples from a target (e.g. organ or tumor) without repeated insertions, with rapid preservation and with minimal variations between different samples, with the ability to reach and monitor various locations within the target.

SUMMARY

The following specification describes a core biopsy system with a curvable core biopsy needle that enables fast and simple acquisition of multiple tissue samples at various locations within a target. The system may include tracking and imaging for optimization of acquiring the multiple tissue samples.

There is provided, in accordance with embodiments of the invention, a core biopsy needle device having a stylet with a curvable elongate member, at least one sample receiving portion at a distal end of the stylet, wherein the curvable elongate member has a stylet curved configuration and a stylet straight configuration, a cutting cannula with an outer curvable elongate member coaxially arranged around the stylet, wherein the curvable outer elongate member has a cutting cannula curved configuration and a cutting cannula straight configuration, wherein the cutting cannula is slidingly movable with respect to the stylet. The device further includes a coaxial needle guide arranged coaxially around and slidable with respect to the stylet and the cutting cannula, wherein when distal ends of the stylet and cutting cannula are positioned within the coaxial needle guide, the stylet is configured in the stylet straight configuration and the cutting cannula is configured in the cutting cannula straight configuration, and when distal ends of the stylet and cutting cannula are positioned distal to the coaxial needle guide, the stylet is configured in the stylet curved configuration and the cutting cannula is configured in the cutting cannula curved configuration. In embodiments of the invention, the stylet and cutting cannula curved configurations have a constant radius of curvature, so that upon entry of the core biopsy needle into body tissue, damage to tissue is avoided.

In accordance with further features in embodiments of the invention, the coaxial needle guide has a pre-curved configuration in an opposite curve direction from the cutting cannula curved configuration and/or the stylet curved configuration, so that when the core biopsy needle is positioned within the coaxial needle guide, the pre-curved configuration of the coaxial needle guide becomes straight. This prevents forces from curved core biopsy needle from bending the coaxial needle guide into a bent configuration when the core biopsy needle is positioned in the coaxial needle guide. In some embodiments, only a distal portion of the coaxial needle guide is pre-curved, while a proximal portion of the coaxial needle guide may be configured with a thickness which is able to withstand forces of the curved core biopsy needle.

In accordance with further features in embodiments of the invention, a motorized control mechanism may be used for controlling movement of the stylet and cutting cannula, including rotational and translational movement, separately and together. In some embodiments, the stylet and cutting cannula are rotationally movable with respect to the coaxial needle guide, and in other embodiments, the entire core biopsy device may be rotated such that the coaxial needle guide rotates along with the stylet and cutting cannula.

There is provided, in accordance with embodiments of the invention, a system for guiding and tracking of a biopsy device during movement of the biopsy device along a curved path within body tissue. The system includes a biopsy device, a tracking system having an imaging component for imaging of the body tissue and a sensing component for sensing of a position of the biopsy device within the body tissue, and a display. The display may include a real-time view of the body tissue (i.e. image derived by the imaging component), a position display for displaying the sensed position of the biopsy device within the tissue at various points in time, and a target display for displaying a projected curved path of the biopsy device, the target display including either a single view with color coding of the position of the projected curved needle path in reference to the image plane, or two or three orthogonal views of the projected curved path.

In accordance with further features in embodiments of the invention, the tracking system provides six degrees of freedom in tracking of the biopsy device. The imaging component may be any suitable imaging system, such as, for example, MRI, CT, ultrasound or others. In accordance with additional features in embodiments of the invention, the system may further include physiological sensors on the biopsy device.

There is provided, in accordance with embodiments of the invention a method of obtaining a biopsy sample. The method includes providing a biopsy device having a curvable core biopsy needle having a stylet and a cutting cannula movable with respect to one another, inserting the biopsy device into a predefined position in the body tissue, advancing the curvable core biopsy needle including both the stylet and the cutting cannula to a target in the body tissue wherein the advancing is done on a curved path, retracting the cutting cannula proximally so as to expose the stylet to the body tissue, advancing the cutting cannula to surround the stylet and cut the sample, and retracting the stylet and cutting cannula proximally. These steps may be repeated multiple times to obtain multiple samples. In embodiments of the invention, the stylet and cannula are advanced through a needle guide. In between each time the steps are repeated, the core biopsy needle may be repositioned—rotationally and/or in a forward direction. Tracking and planning of the positioning of the core biopsy needle may be done as well.

In accordance with further features in embodiments of the invention, the method may include measuring of physiological parameters within the body tissue. Control of the steps of the method may be done using motorized parts.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the invention may be better understood by referring to the following description in conjunction with the accompanying drawings in which:

FIGS. 3A-3F are illustrations of a core biopsy needle device from the system of FIG. 1, in accordance with embodiments of the invention;

Figure 1:
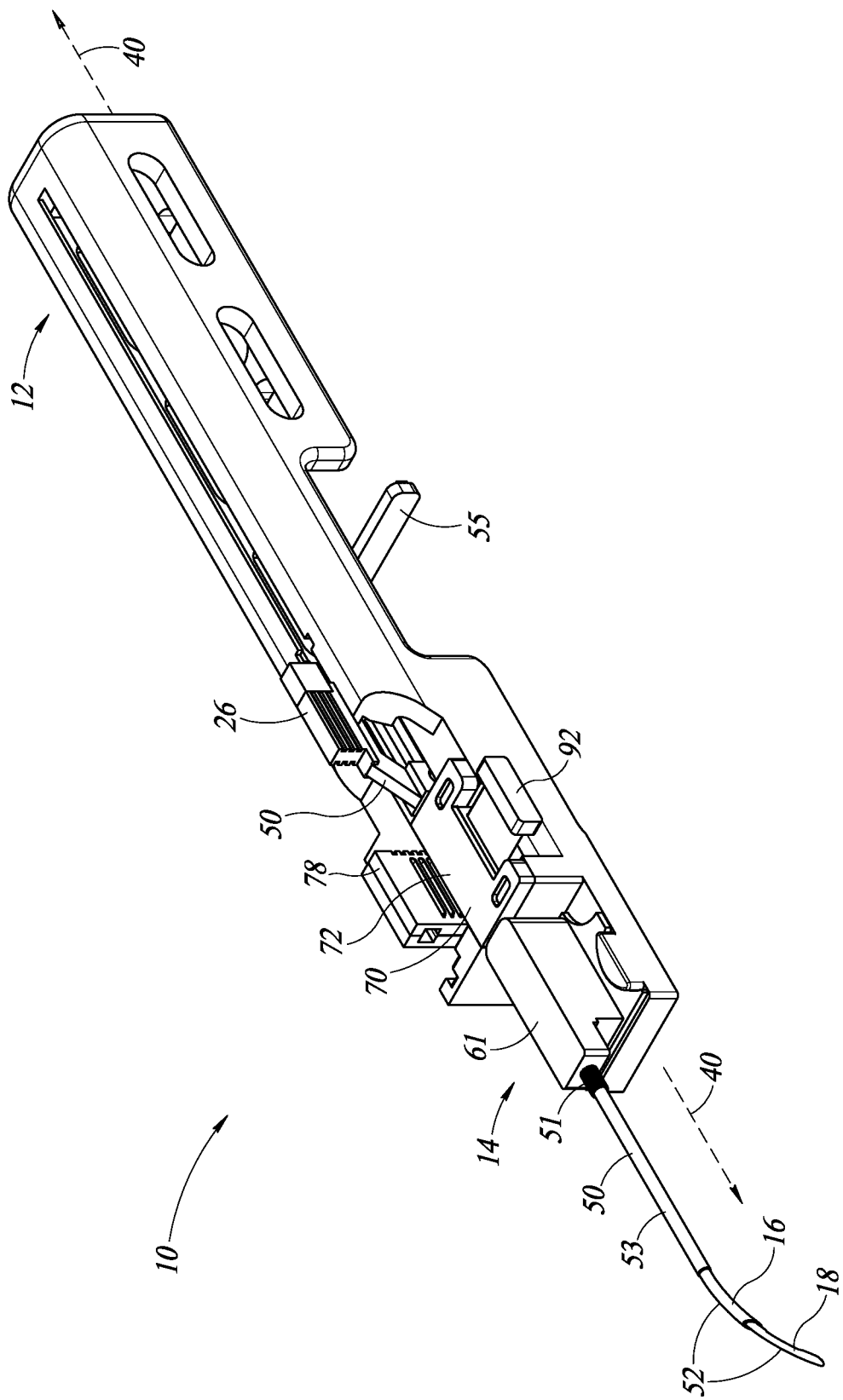
FIG. 1 is a perspective illustration of a core biopsy system in accordance with embodiments of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

Embodiments of the present invention are directed to systems and methods for biopsy and preservation of a tissue sample, and more particularly to a biopsy sample acquisition and tracking system. The system and method of the present invention are designed to provide samples from multiple locations within a target, which can later be used for both microscopic histopathology analysis and biomarker analysis. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Figure 2:
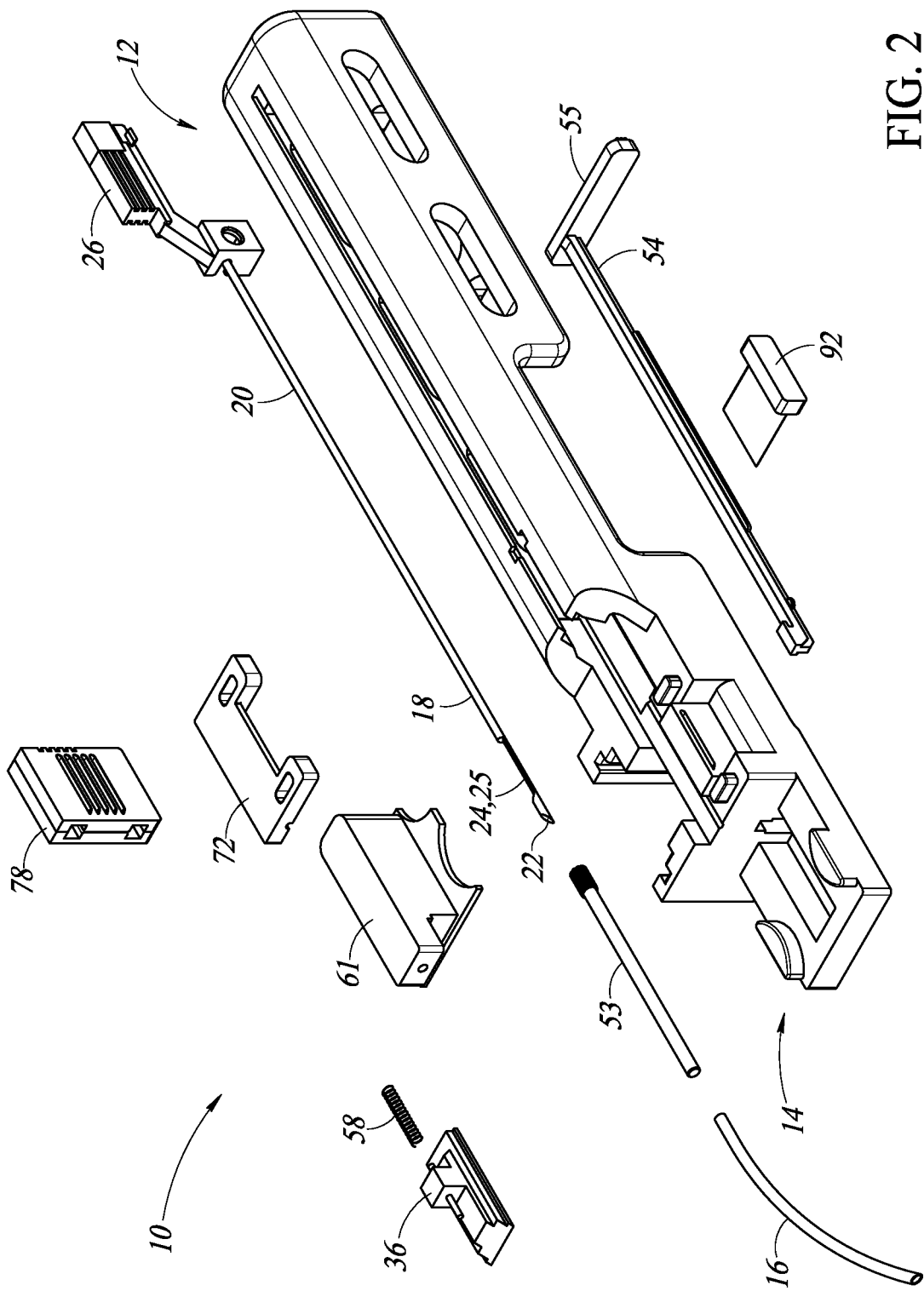
FIG. 2 is an exploded view of the core biopsy system of FIG. 1.

Reference is now made to FIG. 1, which is a perspective illustration of a core biopsy system 10, and to FIG. 2, which is an exploded view of the core biopsy system 10 of FIG. 1, in accordance with embodiments of the present invention. Core biopsy system 10 has a core biopsy system proximal end 12, and a core biopsy system distal end 14, wherein core biopsy system proximal end 12 is defined as the end of core biopsy system 10 which is closer to the user and farther away from the body from which the biopsy sample is to be taken, while core biopsy system distal end 14 is defined as the end of core biopsy system 10 which is farther from the user and closer to the body from which the biopsy sample is to be taken. A longitudinal axis 40 is defined along a length of core biopsy system 10 extending from core biopsy system proximal end 12 to core biopsy system distal end 14.

Core biopsy system 10 includes a core biopsy needle device 50 and a biopsy sample collection device 70. Core biopsy needle device 50 is positioned within biopsy sample collection device 70 and is slidingly movable with respect to biopsy sample collection device 70 along longitudinal axis 40. Biopsy sample collection device 70 includes a sample extractor 92 and a housing 72 and sample cartridge 78, wherein sample extractor 92 is configured to push collected samples into sample cartridge.

Reference is now made to FIGS. 3A-3F, which are illustrations of core biopsy needle device 50, in accordance with embodiments of the present invention. Core biopsy needle device 50 includes a core biopsy needle 52, a coaxial needle guide 53 which is coaxial to core biopsy needle 52, and a firing mechanism 41. Core biopsy needle 52 is a two-part needle including a stylet 18 and a cutting cannula 16 positioned coaxially around stylet 18. Coaxial needle guide 53 is connectable to core biopsy needle device 50 via a needle guide connector 51.

Figure 3C:
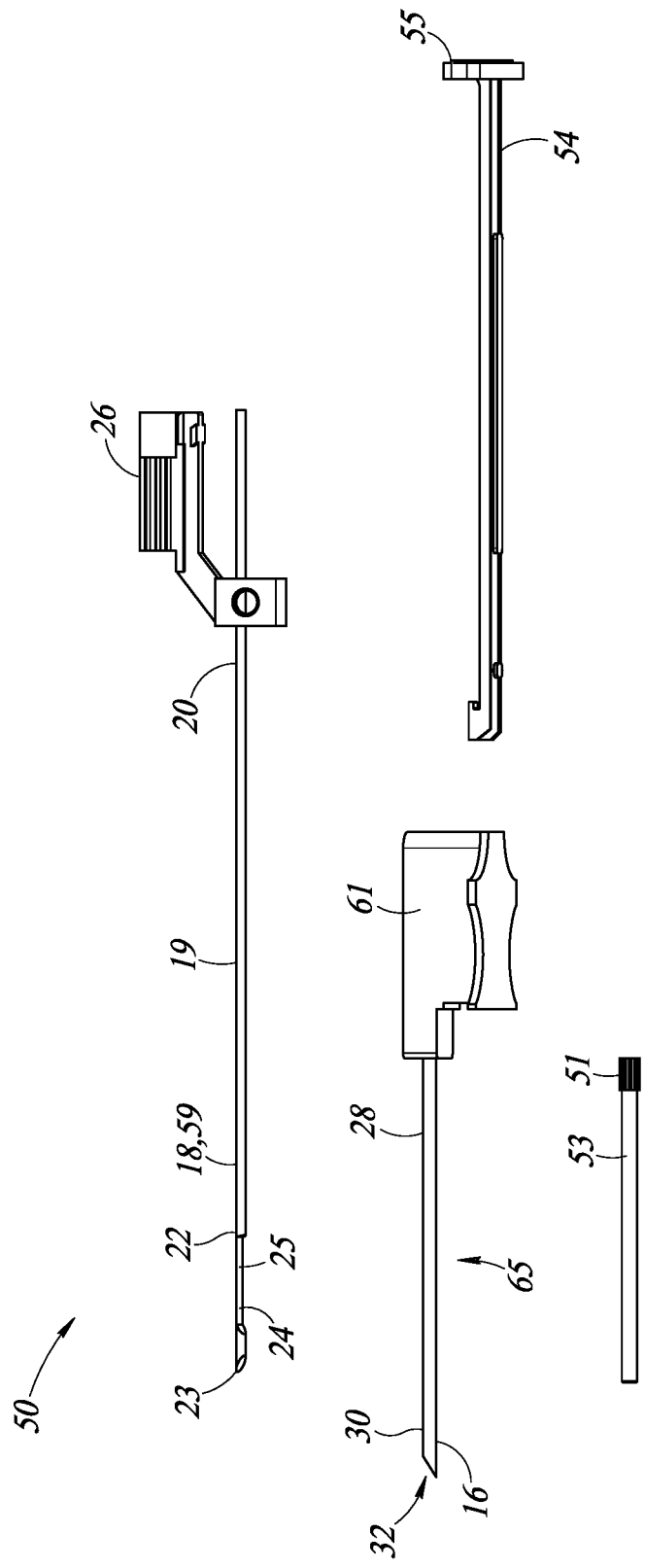

As shown in FIGS. 3A and 3B, respectively, core biopsy needle 52 has a core biopsy needle distal end 48, which may be positioned within coaxial needle guide 53 in a straight configuration or in a curved configuration, as will be explained further hereinbelow. As shown in FIG. 3C, stylet 18 includes a stylet elongate member 19 having a stylet proximal end 20 and a stylet distal end 22, and includes a sample receiving portion 24 at stylet distal end 22.

Figure 3D:
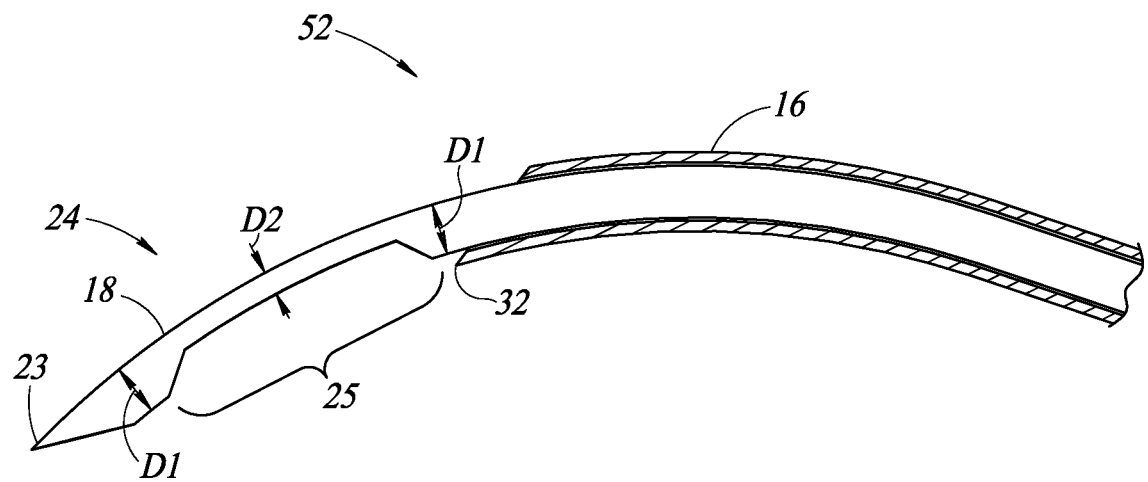

Stylet distal end 22 may further include a sharp tip 23 to enable penetration through skin or other tissue that may be encountered on the way to the target. Sample receiving portion 24 may be, for example, a notch 25 in a portion of the elongate member at stylet distal end 22 as shown in FIG. 3D, resulting in an elongated sample. Notch 25 is a hollowed-out portion of elongate member 19 of stylet 18 which is suitable for holding therein a biopsy sample obtained by cutting cannula 16. In some embodiments, sample receiving portion 24 includes two notches 25 opposite each other for simultaneously holding two biopsy samples. As shown in FIG. 3D, stylet elongate member 19 has a substantially uniform first diameter or thickness D1. This diameter D1 extends along stylet 18 from stylet proximal end 20 until a proximal portion of notch 25, and continues along stylet 18 from a distal portion of notch 25 until sharp tip 23. A specified length (which may be in a range of, but not limited to, 5-20 mm) of stylet 18 has a second diameter or thickness D2 which is less than the first diameter or thickness D1. The smaller second diameter or thickness D2 as compared to the larger diameter D1 creates notch 25 for sample collection.

Stylet 18 further includes a stylet controller 26 at stylet proximal end 20 for pushing stylet 18 distally or pulling stylet 18 proximally as needed. In some embodiments, stylet controller 26 is a handle for manually moving stylet 18 back and forth, as depicted in FIGS. 3A, 3B, 3C, 3E and 3F, for example. In other embodiments, stylet controller 26 is a motorized controller such as an actuator, wherein movement of stylet 18 may be driven by a motor and controlled by a microprocessor or user-operated trigger.

Returning to FIG. 3C, cutting cannula 16 is an elongate member having a cutting cannula proximal end 28 and a cutting cannula distal end 30, and includes a sample cutting portion 32 at cannula distal end 30. Sample cutting portion 32 may be, for example, a blade or sharp edge as is known in the art. In embodiments wherein two notches 25 are used in stylet 18, a two-tip cutting blade can be used so that two samples may be cut simultaneously from the tissue.

Returning now to FIG. 3A, core biopsy needle distal end 48 is contained within coaxial needle guide 53 and as such, core biopsy needle 52 has a straight configuration. In this straight configuration depicted in FIG. 3A, core biopsy needle 52 can be inserted into the body and directed to the target, moved distally and proximally (i.e. forward and backward), and rotated either together with coaxial needle guide 53 or rotated with respect to coaxial needle guide 53 (with the needle guide not rotated), as will be explained further hereinbelow. In the embodiment shown in FIG. 3A, coaxial needle guide 53 is not attached to core biopsy needle device 50, and can be inserted into the body towards the target using image guidance, as is commonly done in current clinical practice of image-guided intervention. Once coaxial needle guide 53 is in place in the body, core biopsy needle 52 is advanced through coaxial needle guide 53 until core biopsy needle 52 is in the desired position. In some embodiments, coaxial needle guide 53 is attached to the core biopsy needle device via a connector 51, such as a Luer lock, for example. In either case, the ability to rotate core biopsy needle 52—either together with coaxial needle guide 53 or with respect thereto—is a key feature that enables the tip of the needle to reach different locations in a volume of interest around the longitudinal axis 40.

As shown in FIG. 3B, when core biopsy needle 52 is deployed distally out of the needle guide 53, a tip of core biopsy needle 52 bends back to its unloaded curved configuration, and as it is further deployed distally out of coaxial needle guide 53, tip 23 of stylet 18 moves farther away from the center of coaxial needle guide 53.

Figure 3E:
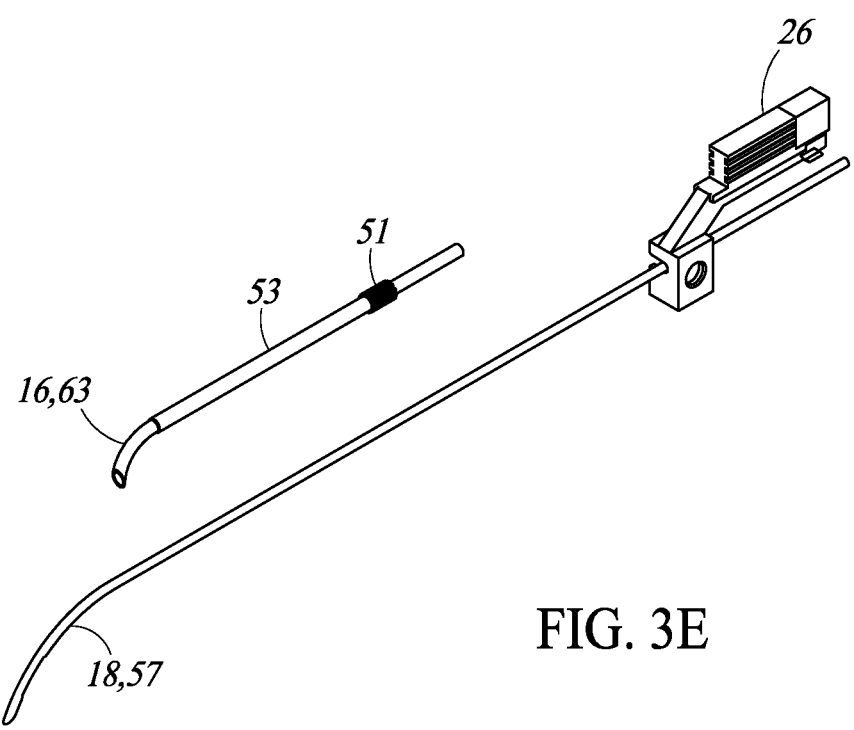

As shown in FIGS. 3A-3F, stylet 18 has two configurations: a stylet curved configuration 57 as shown in FIG. 3B and FIG. 3E, and a stylet straight configuration 59 as shown in FIG. 3A and FIG. 3C. When stylet distal end 22 is positioned within coaxial needle guide 53, stylet 18 has the stylet straight configuration 59. When stylet distal end 22 is positioned outside of coaxial needle guide 53 (i.e., stylet distal end 22 is distal to a distal end of coaxial needle guide 53), stylet 18 has the stylet curved configuration 57, as shown in FIG. 3B and FIG. 3E. Stylet curved configuration 57 may be obtained by forming stylet 18 with superelastic material such as a Nitinol wire, for example, or by other known methods for pre-shaping a superelastic wire. Stylet distal end 22 (including a sharp tip 23 and notch 25, as described below) may be shaped by standard manufacturing methods, for example by milling or by laser cutting.

Cutting cannula 16 has two configurations as well: a cutting cannula curved configuration 63 as shown in FIG. 3B and FIG. 3E, and a cutting cannula straight configuration 65 as shown in FIG. 3C. When cutting cannula distal end 30 is positioned within coaxial needle guide 53, cutting cannula 16 has the cutting cannula straight configuration 65, as shown in FIG. 3C (and as in FIG. 3A—not visible underneath coaxial needle guide 53). When cutting cannula distal end 30 is positioned outside of coaxial needle guide 53 (i.e., cutting cannula distal end 30 is distal to a distal end of coaxial needle guide 53), cutting cannula 16 has the cutting cannula curved configuration 63, as shown in FIG. 3B and FIG. 3E. Cutting cannula curved configuration 63 may be obtained by forming cutting cannula 16 with superelastic material such as a Nitinol tube, for example, or by other known methods for pre-shaping a needle. Cutting cannula distal end 30 with sample cutting portion 32 may be shaped by standard manufacturing methods, for example by milling or by laser cutting.

Figure 3F:
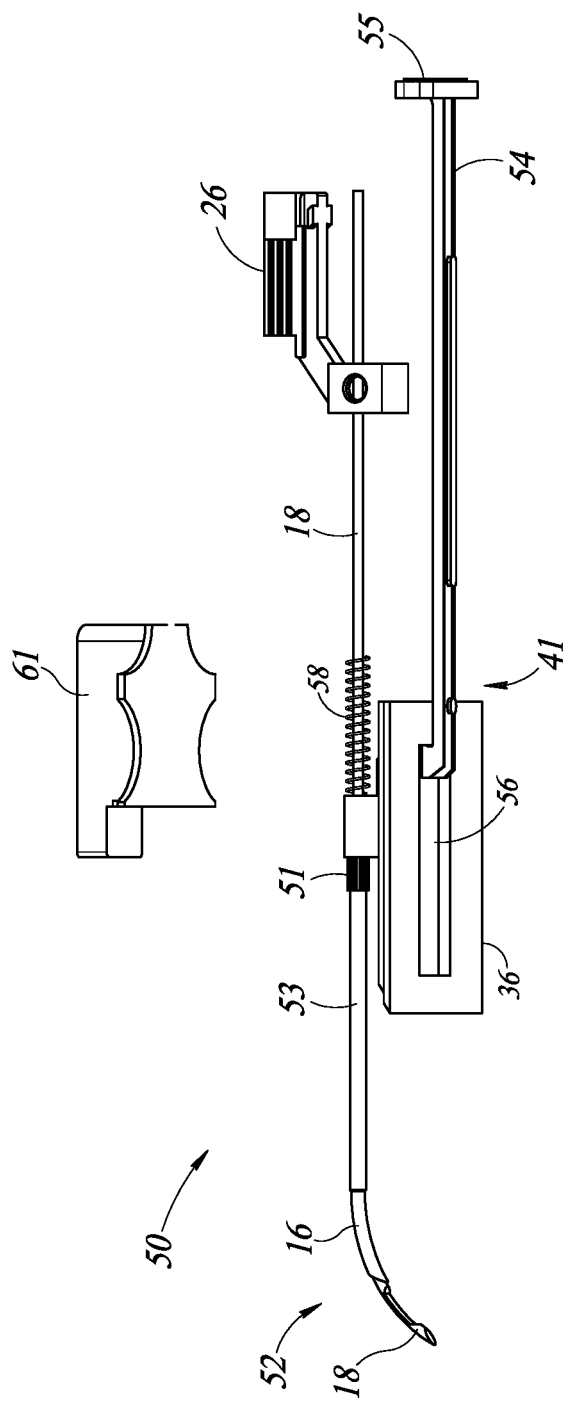

Reference is now made to FIG. 3F, which is an illustration of core biopsy needle device 50 showing firing mechanism 41 in greater detail. Firing mechanism 41 includes trigger arm 54 which is removably hooked into a slider 36, a spring 58 positioned between slider 36 and stylet controller 26 of stylet 18, and enclosure 61 for holding spring mechanism 58 therein. Slider 36 includes a slider slot 56 at a bottom portion thereof for insertion of trigger arm 54. Thus, trigger arm 54 is capable of being positioned at different points along slider slot 56. A trigger handle 55 is connected at a proximal end of trigger arm 54. Stylet 18 is positioned through spring 58.

Enclosure 61 is attached to cannula 16 at cannula proximal end 28. Enclosure 61 is configured to provide a proximal and distal motion of cannula 16 along longitudinal axis 40 to enable cutting of the tissue sample in the notch 25 at the tip 23 of stylet 18.

Trigger arm 54 holds cutting cannula 16 in a proximal position against the resistance of spring 58 by pulling slider 36 into a most proximal position, wherein slider 36 can be latched onto enclosure 61. Such trigger mechanisms are commonly known in the art and are similar to the mechanisms found, for example, in Semi-Automatic Biopsy System (TSK Laboratory, Japan). Other embodiments for firing mechanism 41 are possible as well.

Figure 4A:
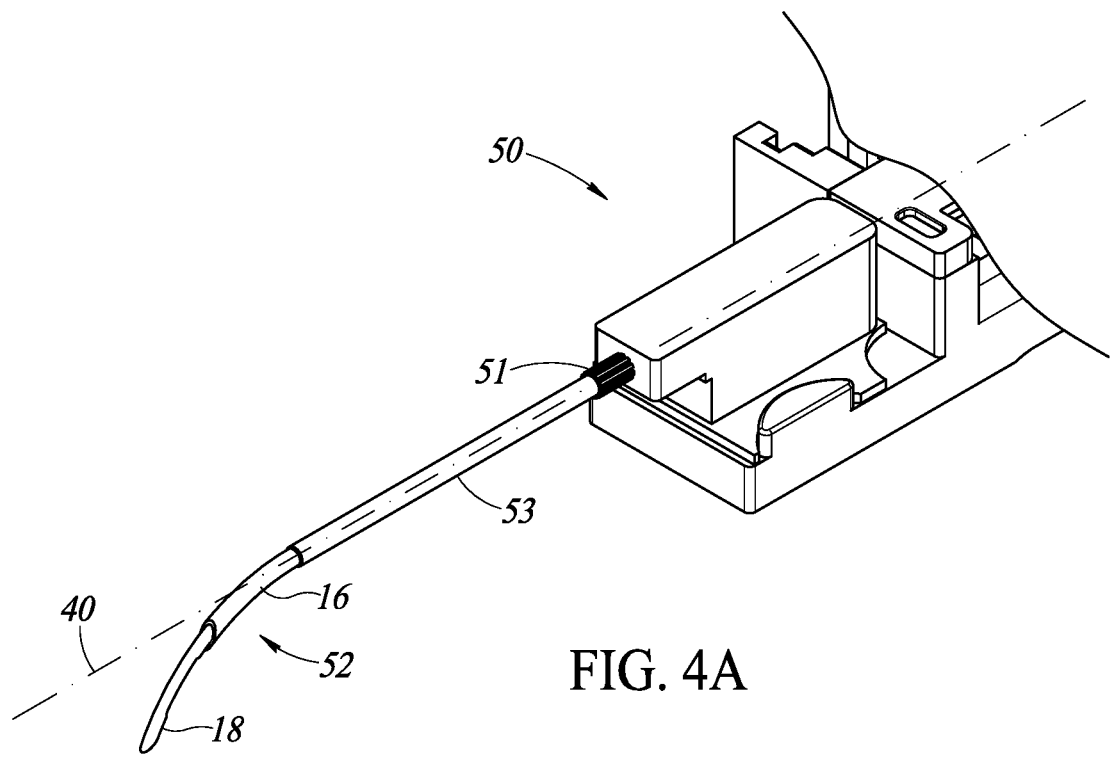
FIGS. 4A and 4B, are illustrations of a distal end of the core biopsy device of FIGS. 1-3, showing a stylet and cutting cannula positioned within a coaxial needle guide and further showing rotation of the core biopsy needle in accordance with embodiments of the invention.
Figure 4B:
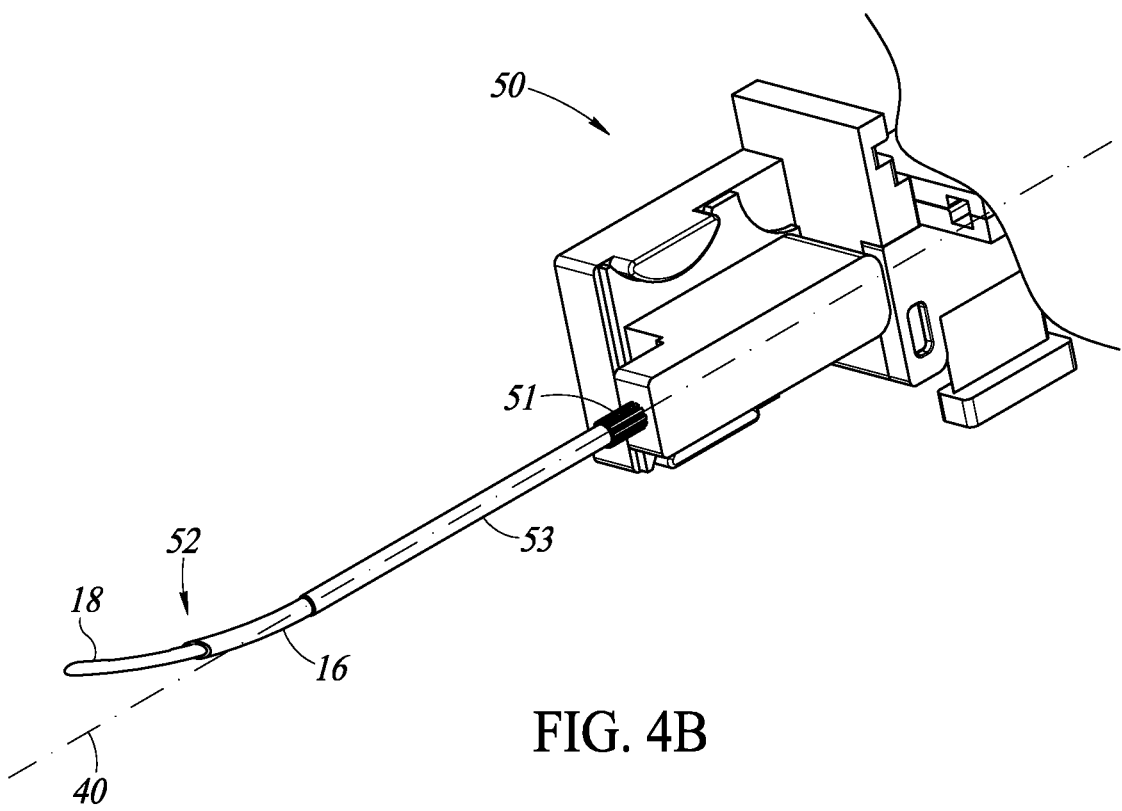

Reference is now made to FIGS. 4A and 4B, which are illustrations of a distal end of core biopsy needle device 50, showing core biopsy needle 52, including both stylet 18 and cutting cannula 16, positioned within coaxial needle guide 53. Coaxial needle guide 53 is configured to rotate about longitudinal axis 40, such that tissue samples may be collected from multiple locations at a particular depth. For example, six cores can be provided for every 60 degree rotation. In one embodiment, the rotational aspect is controlled by rotating core biopsy needle 52 with respect to the coaxial needle guide 53. In another embodiment, an entire core biopsy system 10 can be rotated, as shown in a first position in FIG. 4A and in a second position in FIG. 4B. Rotation can be done when core biopsy needle distal end 48 is contained within coaxial needle guide 53, as shown in FIG. 3A. After rotation to the desired orientation, core biopsy needle 52 is deployed distally out of coaxial needle guide 53 as shown in FIGS. 4A and 4B, for example. As will be described herein below, a tracking system provides the rotation angle of the device and thus the location of the acquired tissue for each sample removed.

Figure 5A:
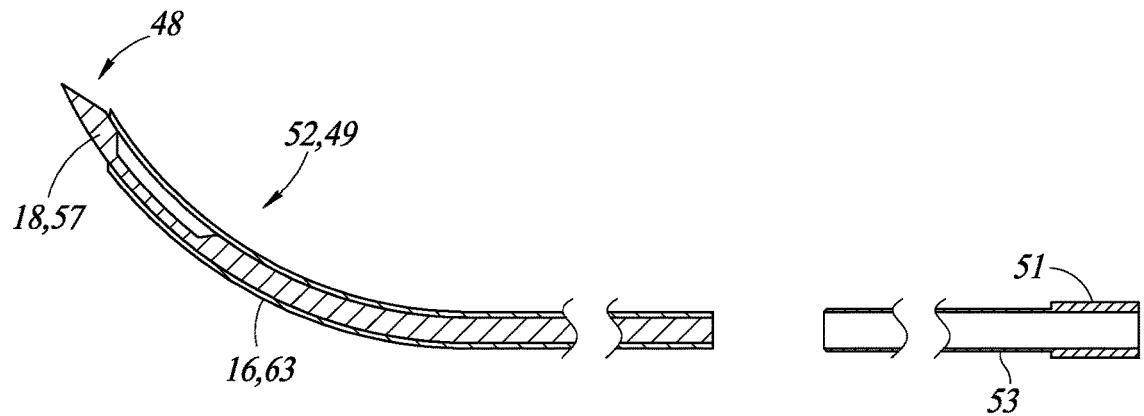
FIGS. 5A-5C are illustrations of the core biopsy needle from the core biopsy device of FIGS. 1-4, showing both the stylet and the cutting cannula in three stages of positioning with respect to the coaxial needle guide.
Figure 5B:
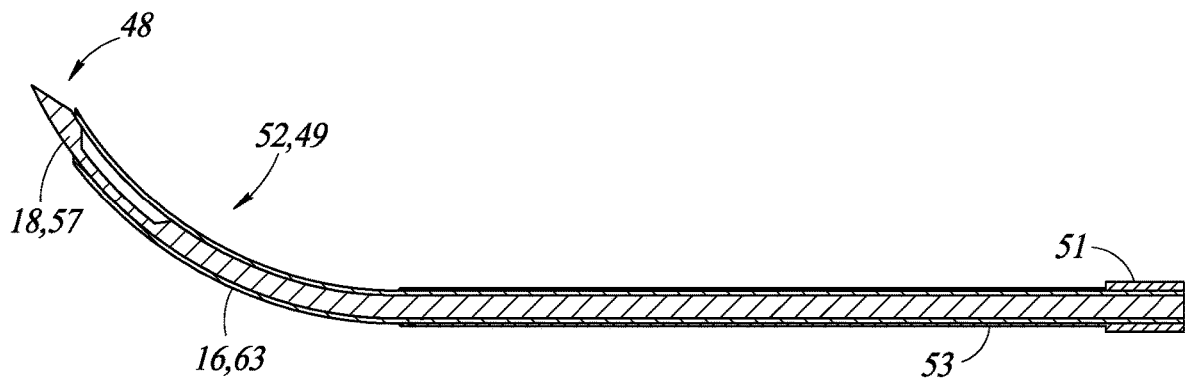
Figure 5C:
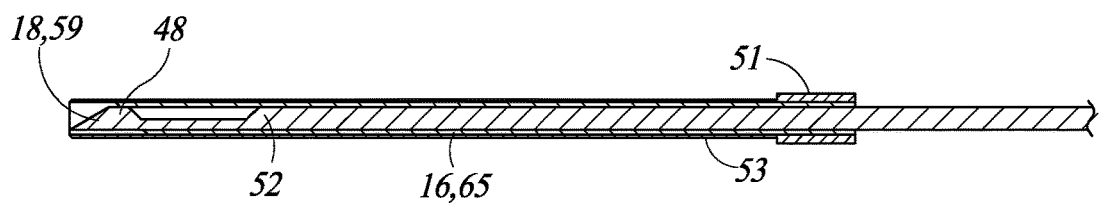

Reference is now made to FIGS. 5A-5C, which are illustrations of core biopsy needle 52, including both stylet 18 and cutting cannula 16, positioned within coaxial needle guide 53 and distal to coaxial needle guide 53. When both stylet 18 and cutting cannula 16 are in their curved configurations (stylet curved configuration 57 and cutting cannula curved configuration 63), core biopsy needle 52 assumes a curved configuration as a whole and is referred to herein as curved core biopsy needle 49. As shown in FIG. 5A, curved core biopsy needle 49 is positioned outside of coaxial needle guide 53, and the curved configuration is apparent, since coaxial needle guide 53 is not holding core biopsy needle 52 therein. In FIG. 5B, curved core biopsy needle 49, 52 is partially surrounded by coaxial needle guide 53, but since core biopsy needle distal end 48 is positioned distal to coaxial needle guide 53, a partial curved configuration is still assumed. As shown in FIG. 5C, when core biopsy needle distal end 48 is positioned within coaxial needle guide 53, core biopsy needle 52 is straight, including straight stylet configuration 59 and straight cutting cannula configuration 65. In embodiments of the invention, curved core biopsy needle 49, including stylet curved configuration 57 and cutting cannula curved configuration 63, may be obtained by pre-shaping stylet distal end 22 and cutting cannula distal end 30 using, for example, a super-elastic material such as Nitinol, such that stylet curved configuration 57 and cutting cannula curved configuration 63 are the unloaded shapes and stylet straight configuration 59 and cutting cannula straight configuration 65 are obtained by "forcing" the straight configuration when stylet distal end 22 and cutting cannula distal end 30 are positioned within coaxial needle guide 53.

In another embodiment, curved core biopsy needle 49 may be formed by using a deflectable needle guide (instead of straight biopsy needle guide 53) with a distal end that can be angulated with a tension cable, and a straight superelastic core biopsy needle 49 that can be flexed by pulling on the tension cable of the steerable guide. Such a curved core biopsy needle 49 can be steered to targets away from the needle shaft. Other methods are possible as well and are included within the scope of the invention.

Figure 6A:
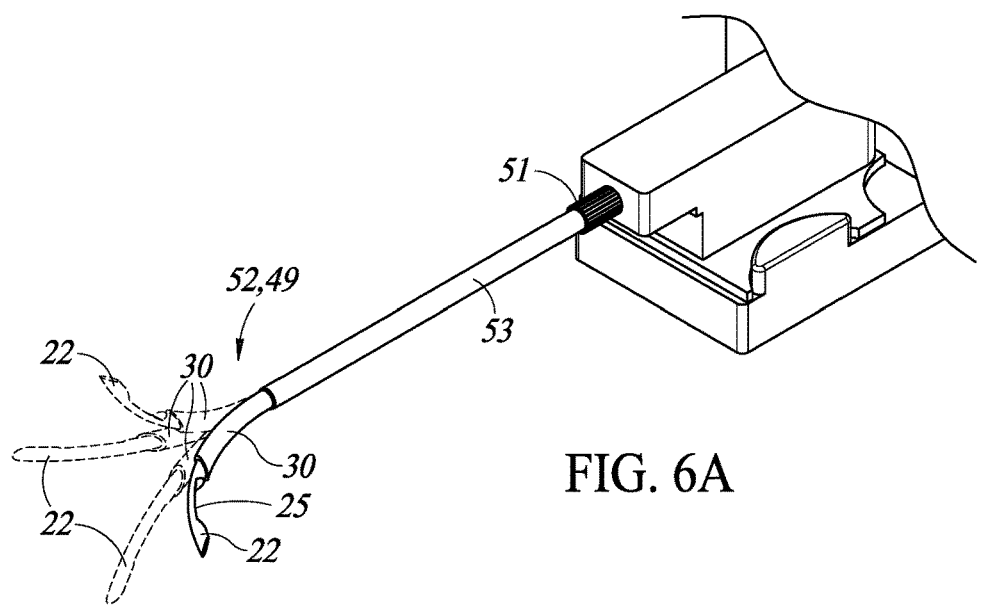
FIGS. 6A-6C are illustrations of the core biopsy needle from the core biopsy device of FIGS. 1-4, showing both the stylet and the cutting cannula positioned within the coaxial needle guide and further depicting the combined effects of the curved configuration of the core biopsy needle, the rotational movement of the core biopsy needle, and forward deployment of the core biopsy needle from the coaxial needle guide, in accordance with embodiments of the present invention.
Figure 6B:
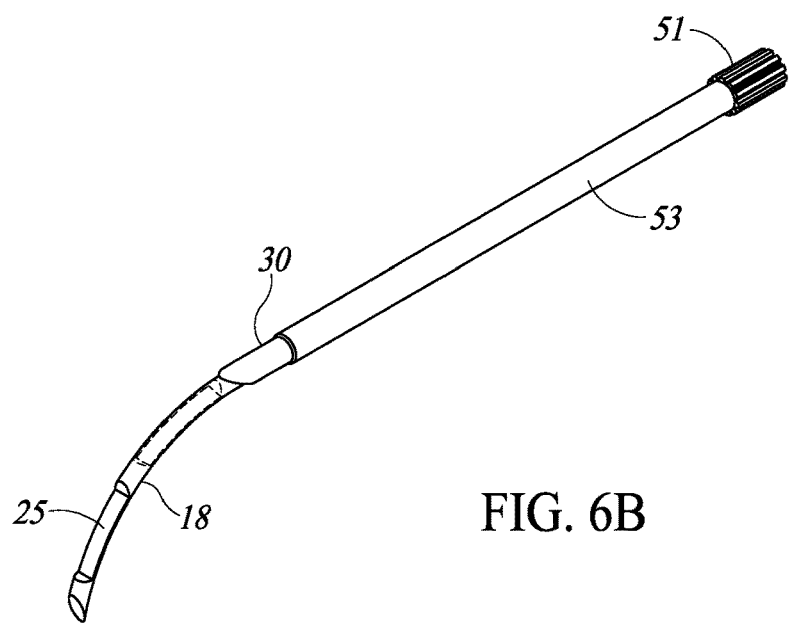
Figure 6C:
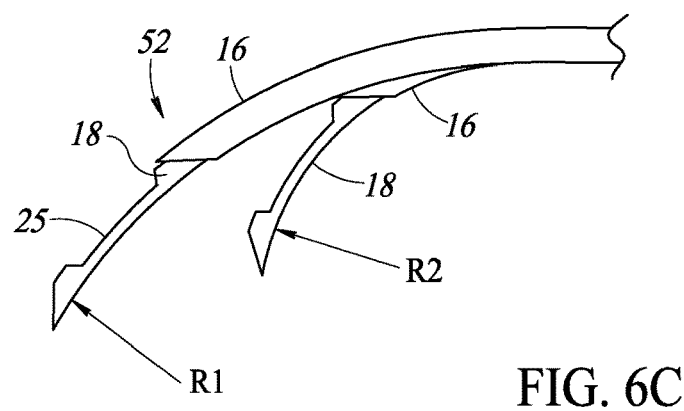

Reference is now made to FIGS. 6A-6C, which are illustrations of curved core biopsy needle 52, 49, showing the different orientations that can be obtained through the combined use of rotation and forward motion, taken together with the curved configurations of curved core biopsy needle 52, 49. As shown in FIG. 6A, when curved core biopsy needle 52, 49 including both stylet distal end 22 and cutting cannula distal end 30 are positioned distal to coaxial needle guide 53, core biopsy needle 52 assumes the curved core biopsy needle 49 configuration, and rotation of core biopsy needle 52, 49 provides access to multiple locations at a range of 360 degrees. Curved core biopsy needle 52, 49 is shown in multiple positions rotationally in FIG. 6A. Rotation may be accomplished by rotating core biopsy needle 52 with respect to coaxial needle guide 53. Alternatively, an entire core biopsy needle device 50 may be rotated from outside of the body. As shown in FIG. 6B, stylet 18 may be deployed distally out of coaxial needle guide 53 by different amounts, leading to different locations away from coaxial needle guide 53. Stylet 18 is shown in FIG. 6B in two different positions as a schematic depiction of the many different possible distally deployed positions of core biopsy needle 52 with respect to coaxial needle guide 53. It should be readily apparent that in embodiments of the invention, cutting cannula distal end 30 accompanies stylet 18 in its forward deployment. By combining the rotation of core biopsy needle 52 within the needle guide 53 (as shown in FIG. 6A), different positions (i.e. depth within the tissue) of coaxial needle guide 53, and different amount of deployment of core biopsy needle 52 from coaxial needle guide 53 (as shown in FIG. 6B), the tip of the stylet (with notch 25, where the tissue sample is acquired) can be directed to any position around coaxial needle guide 53, and a tissue sample can be acquired at many different locations within the target (e.g. tumor). This feature of combined rotation, translation and distal needle deployment provides complete coverage of tissue volume around core biopsy needle 52. As shown in FIG. 6C, an alternative method to control the radial distance of the notch 25 with respect to the shaft of the coaxial needle guide 53 is to use core biopsy needles 52 with different radii of curvature. As shown in FIG. 6C, a core biopsy needle 52 having a first radius of curvature R1 will advance farther away radially from coaxial needle guide 53 than a core biopsy needle 52 having a second radius of curvature R2 which is smaller than the first radius of curvature R1. Thus, the needle radius of curvature can be used as a design parameter of core biopsy needle 52 to allow the use of different needles to penetrate through different paths to the target. Such variations in design can be used to enable biopsy sampling "around a corner" in cases where direct line of penetration to the target cannot be achieved due to anatomic constraints. It is a feature of the present invention that the radius of curvature of any given core biopsy needle 52 used in the present invention (R1 or R2 or any Rn) is constant. That is, the shape of the curved core biopsy needle 52, 49 is a circular arc. This minimizes damage to the surrounding tissue.

As such, it is readily apparent that an unlimited number of locations for obtaining tissue samples is available using the device of the present invention.

Figure 7A:
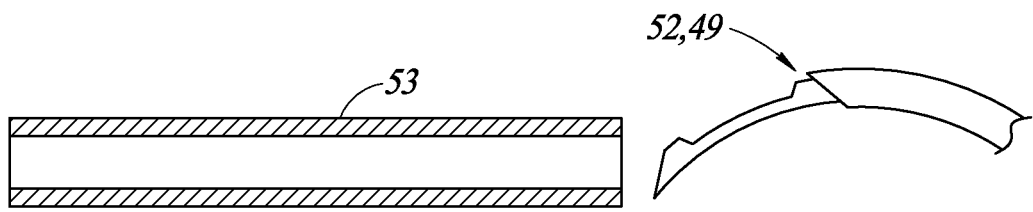
FIGS. 7A and 7B are schematic illustrations of a coaxial needle guide, depicting forces that may be generated by the coaxial needle guide on a curved core biopsy needle positioned therein.
Figure 7B:
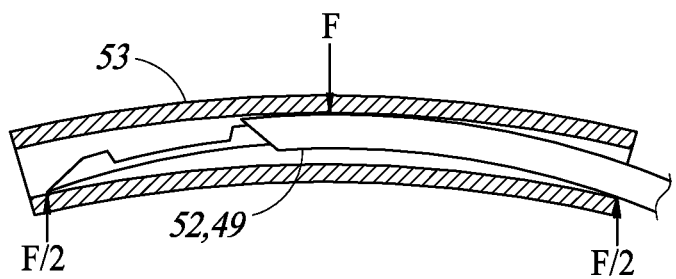

One problem that may arise with the use of a curved core biopsy needle 52, 49, is that the coaxial needle guide 53 may become bent due to forces exerted by the curved core biopsy needle 52, 49 on coaxial needle guide 53 when core biopsy needle 52 is positioned therein. As shown in FIGS. 7A and 7B, forces (F, F/2) that are generated by bending of core biopsy needle 52 when it is inserted into the straight coaxial needle guide 53 can cause counter-bending of the coaxial needle guide 53. This could be problematic since in the present invention multiple insertions and retractions are performed, and more significantly, rotation is performed within the body as well. These actions may cause damage to surrounding tissue if coaxial needle guide 53 is bent. Thus, it is important to have a straight coaxial needle guide 53. One way of solving this problem would be to use a very rigid needle guide. However, when very thin needles must be used, typically for intervention into organs with high vasculature (e.g. liver) or critical structures (e.g. brain), a rigid needle guide will increase the needle size too much. Thus there is a need for a solution for a thin walled needle guide.

Figure 8A:
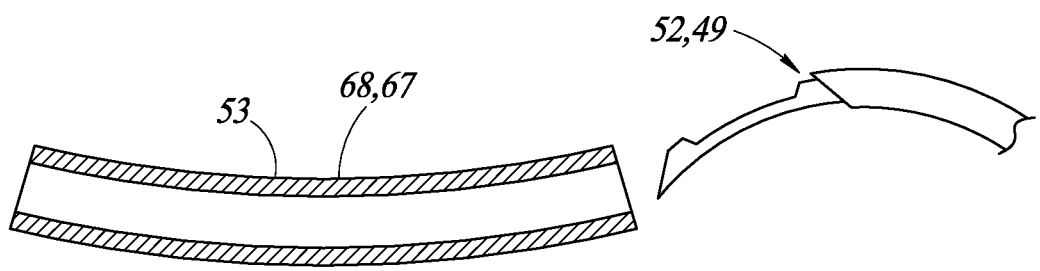
FIGS. 8A and 8B are schematic illustrations of a pre-curved needle guide, in accordance with embodiments of the present invention.
Figure 8B:
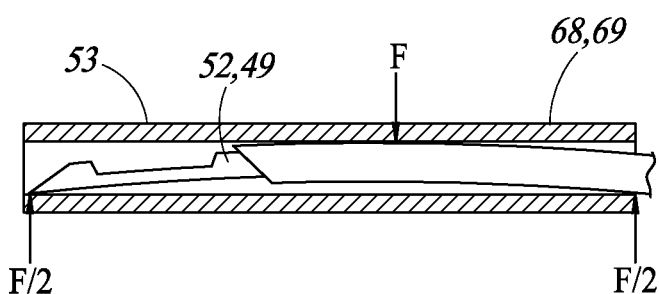

One solution to this problem is depicted in FIGS. 8A and 8B, which are illustrations of a pre-curved needle guide 68 having a needle guide curved configuration 67 and a needle guide straight configuration 69, in accordance with embodiments of the present invention.

Pre-curved needle guide 68 has a slightly curved configuration 67, such that when core biopsy needle 52 is pulled into pre-curved needle guide 68, it may be positioned such that the interaction forces between the straightened biopsy needle 52 and the pre-curved needle guide 68 acting on pre-curved needle guide 68 straighten it out rather than cause a bend. Essentially, it corrects the pre-curved bend to obtain a straight configuration 69.

The pre-bent shape of pre-curved needle guide 68 is designed to take into account the dimensions of core needle guide 53 and the mechanical properties of its material, as well as the anticipated forces that will be generated by the loaded curved core biopsy needle 52, 49 inside the pre-curved needle guide 68. Typically, the coaxial needle guide 53 will be made of more rigid material (e.g. stainless steel) compared with the superflexible Nitinol of core biopsy needle 52. Thus the needle guide should have a smaller extent of pre-curving compared with the circular unloaded shapes of core biopsy needle 52.

Figure 9A:
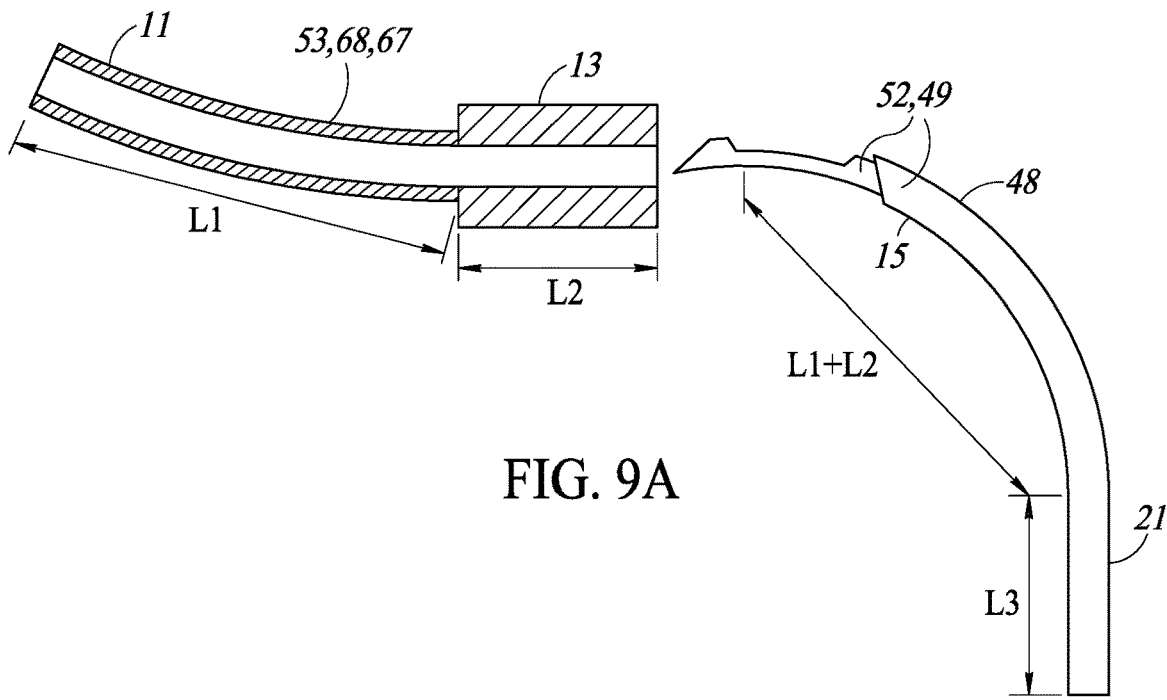
FIGS. 9A-9C are schematic illustrations of a pre-curved needle guide having a curved distal portion and a straight proximal portion, in accordance with additional embodiments of the present invention.
Figure 9B:
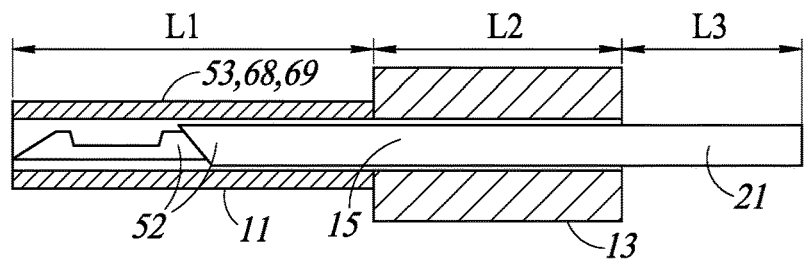
Figure 9C:
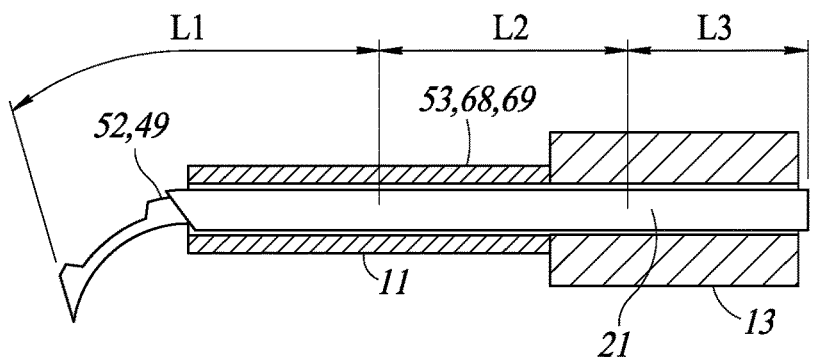

Reference is now made to FIGS. 9A-9C, which are illustrations of pre-curved needle guide 68, in accordance with additional embodiments of the present invention. Since in some embodiments a curved portion of curved core biopsy needle 52, 49 is only at a curved core biopsy needle distal end 48, when curved core biopsy needle 52, 49 is pushed distally past coaxial needle guide 53, 68, and the straight portion of curved core biopsy needle 52, 49 is now in coaxial needle guide 53, 68, coaxial needle guide 68 may resume its curved configuration 67. However, sometimes there is a need to maintain coaxial needle guide 53 in a straight configuration when the curved core biopsy needle 52, 49 is deployed distally from coaxial needle guide 53. In the embodiment shown in FIG. 9A, pre-curved needle guide 68 includes a pre-curved distal portion 11 with length L1 and a straight proximal portion 13 with length L2. Straight proximal portion 13 is a thick-walled tube, which is not deformed by the curve of curved core biopsy needle 52, 49. The thick-walled tube has a thickness which is sufficient to prevent bending under forces F and F/2 of curved core biopsy needle 52, 49. Length L2 of straight proximal portion 13 is at least the amount of potential distal deployment of core biopsy needle 52. For example, if core biopsy needle 52 is deployable for a distance of up to 25 mm, straight proximal portion 13 has a length L2 of at least 25 mm.

Curved core biopsy needle 52, 49 has a distal curvable portion 15 which equals the length L1+L2 of pre-curved needle guide 68, including both the straight proximal portion 13 and the curved distal portion 11 of pre-curved needle guide 68 (i.e. the thin walled portion and the thick walled portion). Curved core biopsy needle 52, 49 also has an additional proximal portion 21 which is equal to the length L3 of potential distal deployment (e.g. 25 mm from the non-limiting example above). L2 is thus greater than or equal to L3. This additional proximal portion 21 may be curved or straight. When the curved core biopsy needle 52, 49 is fully inserted into coaxial needle guide 53, 68, the proximal portion 21 of curved core biopsy needle 52, 49 remains out of the needle guide, as shown in FIG. 9B. When curved core biopsy needle 52, 49 is fully deployed distally to its maximum deployment, as in FIG. 9C, the proximal portion 21 lies within the straight proximal portion 13 of coaxial needle guide 68, 53. Thus, the pre-curved distal portion 11 of coaxial needle guide 68, 53 (which is the thin-walled part) holds the distal curved portion of curved core biopsy needle 52, 49, and maintains a straight configuration via pre-bending, as described above with respect to FIG. 8B, while straight proximal portion 13 remains straight as well due to its thickness. Thus, the entire pre-curved needle guide 68 remains straight during deployment.

Pre-curved needle guide 68 can be useful in many different clinical applications, including aspiration of biopsy cells or tissue—with multiple samples taken from an organ, as in the present application, but may also be useful for ablation of a target volume by heating or by freezing or for injection of a substance (for example drug) into a specific location in the target volume or for targeting an area that is located at a radial distance from the penetration line of the needle.

Position Tracking System

Figure 10:
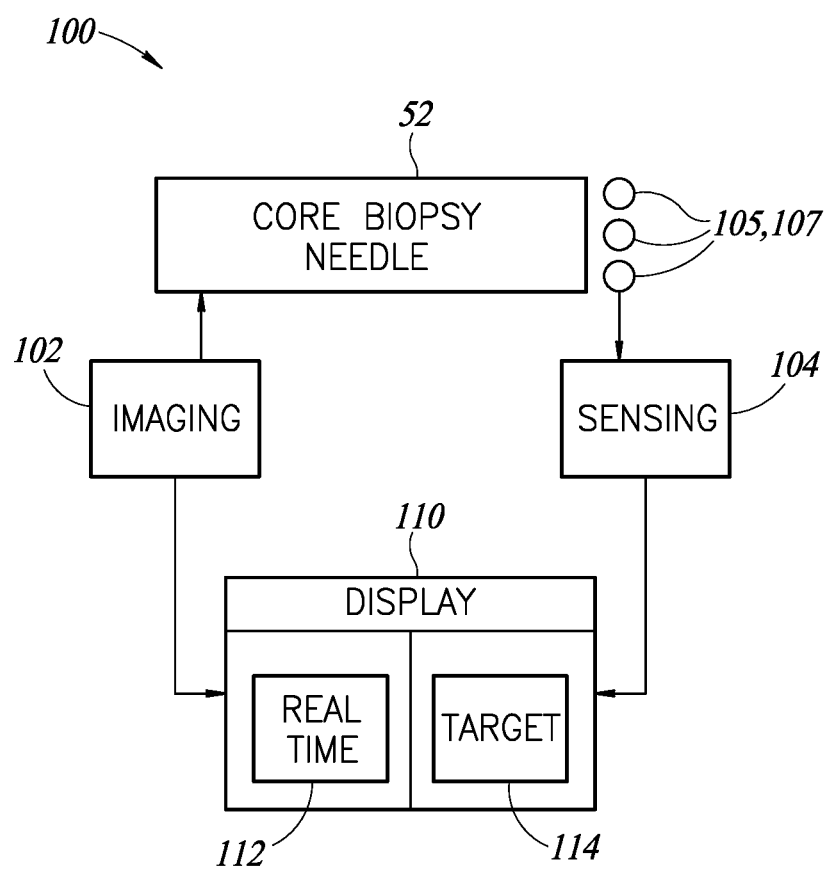
FIG. 10 is a block diagram illustration of a position tracking system, in accordance with embodiments of the present invention.

In embodiments of the present invention, a position tracking system 100 is provided to allow a user to accurately direct core biopsy needle 52 to targets in radial positions away from a needle insertion path and to register tissue acquisition sites on images of the biopsied organ. Reference is now made to FIG. 10, which is a block diagram illustration of position tracking system 100, in accordance with embodiments of the present invention. Position tracking system 100 includes an imaging component 102 for imaging of the body tissue, a sensing component 104 for sensing a position of core biopsy needle 52 within the body tissue, and a display 110.

Imaging component 102 may be, for example, MRI, CT, ultrasound, or any other suitable imaging system. A system for tracking a device such as a biopsy device using MRI gradient fields is the EndoScout® Tracking System (Robin Medical Inc., Baltimore, MD). The EndoScout® Tracking System uses gradient fields of an MRI scanner to determine positioning of a device such as a biopsy needle in reference to MR images. In some embodiments that are based on non-MRI imaging (e.g. ultrasound, CT, X-ray), a tracking system such as the Aurora electromagnetic tracking system by Northern Digital Inc. (Waterloo, Ontario, Canada) can be used similarly to the use of the EndoScout in MRI-guided interventions.

Sensing component 104 may include one or more tracking sensors 105 attached to core biopsy needle 52. Tracking sensor 105 provides the position and orientation of core biopsy needle 52. By knowing the position and orientation of the biopsy needle guide 53, the curvature of the curved core biopsy needle 52, 49 (after it is advanced through coaxial needle guide 53, 68), and the planned length of forward deployment of curved core biopsy needle 52, 49 out of coaxial needle guide 53, it is possible to calculate the future position of the stylet's notch 25 within a target and to provide a projected needle trajectory to this position. After harvesting of a sample, a harvested sample position may be registered as well. Since in the present invention, multiple samples are taken from multiple locations, there will be multiple harvested sample positions.

In addition to tracking sensor 105, core biopsy needle 52, 49 may also include one or multiple physiological sensors 107. Physiological sensors 107 may be, for example, one or multiple fiberoptic sensors for sensing of physiologic and/or physical parameters. Parameters measured by physiological sensors 107 and by tracking sensors 105 may be registered during the advancement of core biopsy needle 52 at any given instantaneous position of core biopsy needle 52, and thus provide the parameters' distribution along each penetration path in the tumor. These distributions can be further processed with the 3D imaging data of the tumor to provide the 3D estimated distributions of these physiologic and physical parameters within the tumor. Tracking sensors 105 and physiological sensors 107 thus have an integrated ability to monitor physiological and physical parameters in the tissue. In one embodiment, physiological sensors 107 are optical fibers embedded within core biopsy needle 52. These fibers enable measurement of pH, oxygen saturation, tissue force (which will enable estimation of tissue stiffness) and potentially other properties. Such measurements can be used to verify accurate placement of the needle tip in the target (e.g. pH level can be lower within the tumor, compared with normal tissue, due to insufficient oxygen supply to the tumor). Physical properties of the tumor can be measured for each core position, before tissue is cut, and along the path of needle insertion to the target.

Graphic User Interface

Figure 11:
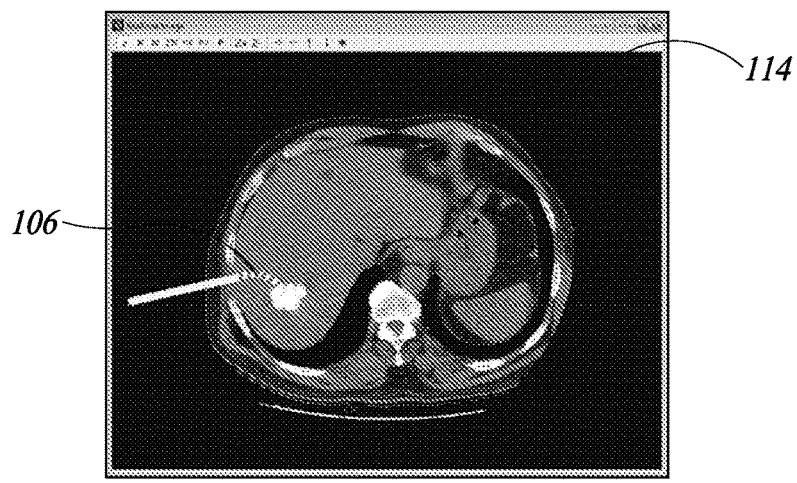
FIG. 11 is an example of a target display from the position tracking system of FIG. 10.

A particular feature of the present invention is display 110, designed to present real-time position and orientation of core biopsy needle 52, 49 (as provided by position tracking system 100) as well as a projected target. Display 110 includes a real-time position display 112 and a target display 114. Target display 114 may include an image of the target tissue and presentation of a projected needle trajectory, which may be a curved path of core biopsy needle 52, 49. An example of target display 114 is shown in FIG. 11. A projected needle trajectory 106 is based on the current position and orientation of core biopsy needle 52, 49, the length of deployment of stylet 18 and cutting cannula 16 with respect to coaxial needle guide 53, the radius of curvature of core biopsy needle 52, and the circumferential rotation angle of the curved core biopsy needle 52, 49 in relation to coaxial needle guide 53, each of which may be set by the user.

Figure 12A:
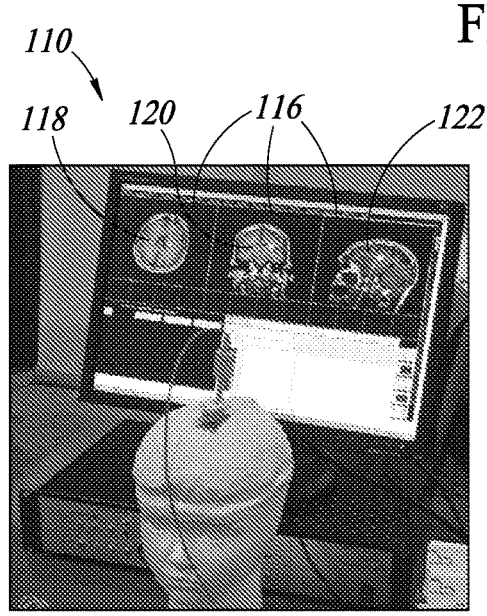
FIGS. 12A and 12B are illustrations of a display including images acquired from an imaging component of the position tracking system of FIG. 10.
Figure 12B:
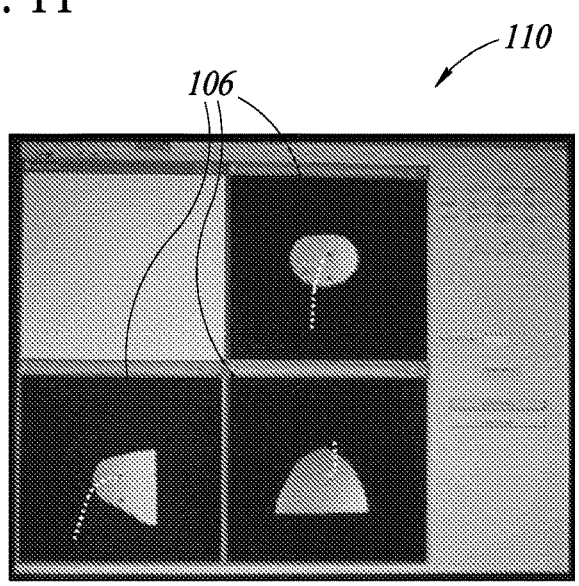
Figure 13:
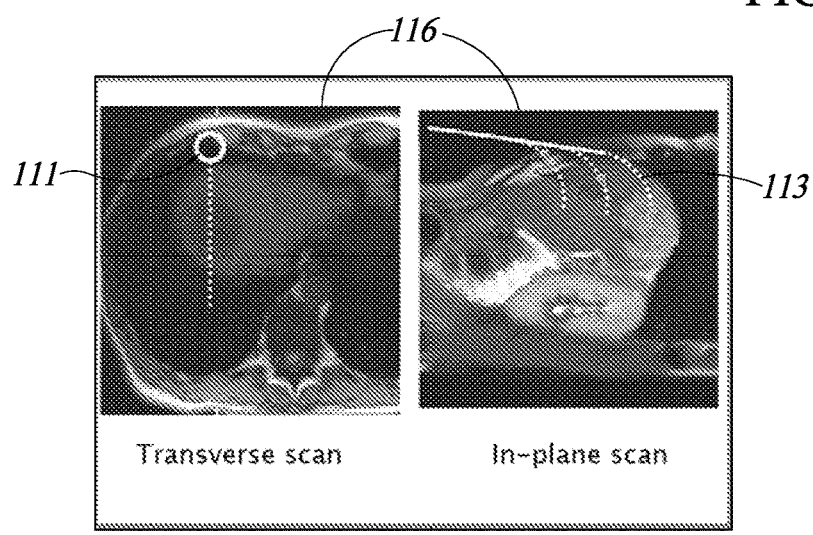
FIG. 13 is an illustration of a display including two orthogonal images acquired from an imaging component of the position tracking system of FIG. 10 in accordance with additional embodiments of the present invention.

Reference is now made to FIGS. 12A and 12B, which are illustrations of display 110 in accordance with embodiments of the present invention. Display 110 includes images 116 acquired from imaging component 102. Images 116 are obtained in multiple planes for optimal visualization and positioning. As shown in FIG. 12A, images 116 are provided in a first plane 118, a second plane 120 which is transverse to first plane 118 and a third plane 122 which is transverse to first plane 118 and to second plane 120. These images 116 can be reconstructed, for example, from high resolution 3D MRI scan that is done at the start of the procedure to identify the target and critical structures around it; or, for example, by multiplanar reconstruction of high-resolution axial CT scans. Real-time tracking data from tracking sensor 105 are overlaid over images 116. Projected needle trajectory 106 is also provided and overlaid over images 116, as shown in FIG. 12B. By obtaining at least two, and in some embodiments three, orthogonal views, projected needle trajectory 106 may be calculated while taking into account the curved path. Projected needle trajectory 106 may include both a calculated insertion point 111 as well as a calculated path 113 to the target, as shown in FIG. 13. An in-plane scan (i.e. a scan through the needle insertion path) with overlaid tracking annotation may also be used for real-time monitoring of the procedure.

The planning mode enables the user to choose the entry point and orientation of the device in order to reach the target through a safe path, avoiding critical structures like large blood vessels, the GI tract, nerve bundles and others. With the device placed in the entry point, if the intervention is conducted under realtime MRI scanning or ultrasound imaging, where scanning planes can be done in any orientation, tracking system 100 provides the required data to set an in-plane realtime scan plane that includes the target and the projected needle path. Such in-plane scan enables monitoring of the device when it is entered to the target.

Reference is now made to FIG. 13, which is an illustration of display 110 in accordance with embodiments of the present invention. Display 110 includes two orthogonal images 116. In the example shown herein, one scan (shown on a left side of FIG. 13) is in a transverse (perpendicular to the needle orientation) plane, and shows an insertion point 111, while the other scan (shown on a right side of FIG. 13) is the in-plane scan that shows the calculated path 113 at different times during the insertion process. FIGS. 13A and 13B depict the dynamics of needle insertion. However, it should be readily apparent that in practice, the insertion point may not be depicted and only the projected path may be depicted for purposes of guidance. A solid line (nondashed) depicts the curved core biopsy needle 52, 49 within the coaxial needle guide 53, and a dashed line depicts the future curved core biopsy needle 52, 49 trajectory when it is deployed out of the coaxial needle guide 53. In this way, real-time annotation may be updated during the insertion process of core biopsy needle 52.

The above-example was shown for an MRI imaging system. Other imaging modalities may require slightly modified user interfaces according to their specific imaging characteristics. For example, ultrasound typically provides a planar scan, although 3D scanners are available. For a trans-rectal ultrasound (TRUS) prostate biopsy the coaxial needle guide 53 may be attached to a hand-held scanning probe, and the needle insertion direction may be limited to the scanning plane of the probe. Thus the user will be able to plan the needle insertion in the imaging scan plane and get real-time image with overlaid tracking annotation. Rotation of the probe can be done with the needle guide serving as the axis of rotation in order to enable access to all targets in the volume of interest of the gland.

CT guidance is typically based on axial scans and not on in-plane scans as in MRI. After proper registration of the tracking system and the CT scanner, tracking annotation can be added to each axial scan and enable the operator to plan and monitor the biopsy procedure with the curved needle.

Thus, the position of each harvested tissue core within the tumor is determined by tracking the 6-degrees of freedom (DOF) position of core biopsy needle 52 with a tracking system, and by knowing the 3D shape of the tissue acquisition needle that is pushed forward into the tissue. The device of the present invention is usable under all routine image-guidance modalities, including X-ray, CT, Ultrasound and MRI.

As shown in FIGS. 14A-D and 15A-E, respectively, there are two potential approaches to operating core biopsy system 10: an exposed stylet method 200, as shown in FIGS. 14A-D, and a sheathed stylet method 300, as shown in FIGS. 15A-E.

Figure 14:
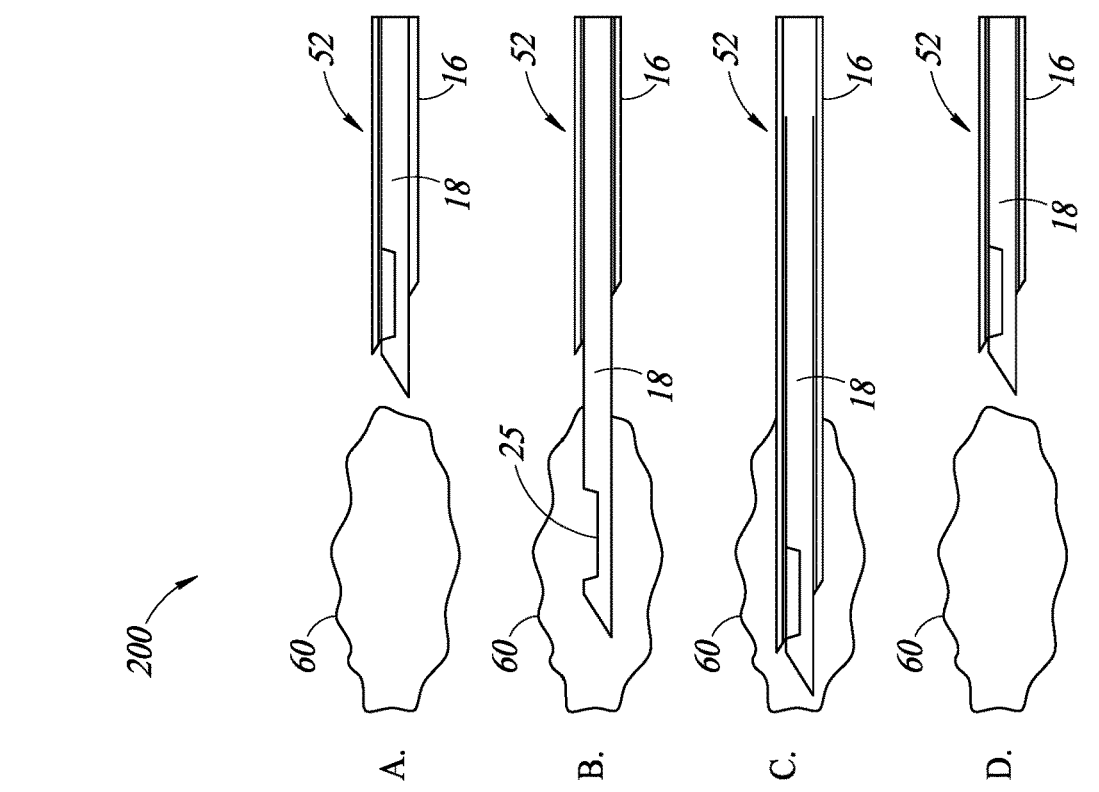
FIGS. 14A-D are schematic representations of an exposed stylet method of obtaining a biopsy sample.

In the exposed stylet method 200, first stylet 18 and cutting cannula 16 are provided (FIG. 14A). Stylet 18 is advanced to a target 60 without cutting cannula 16 by pushing stylet 18 distally with respect to cutting cannula 16 (FIG. 14B). Once stylet 18 is in place in target 60, and notch 25 has a tissue sample therein, cutting cannula 16 is fired distally to cut the tissue sample (FIG. 14C). Finally, stylet 18 and cutting cannula 16 are retracted together and the sample is removed (FIG. 14D).

Figure 15:
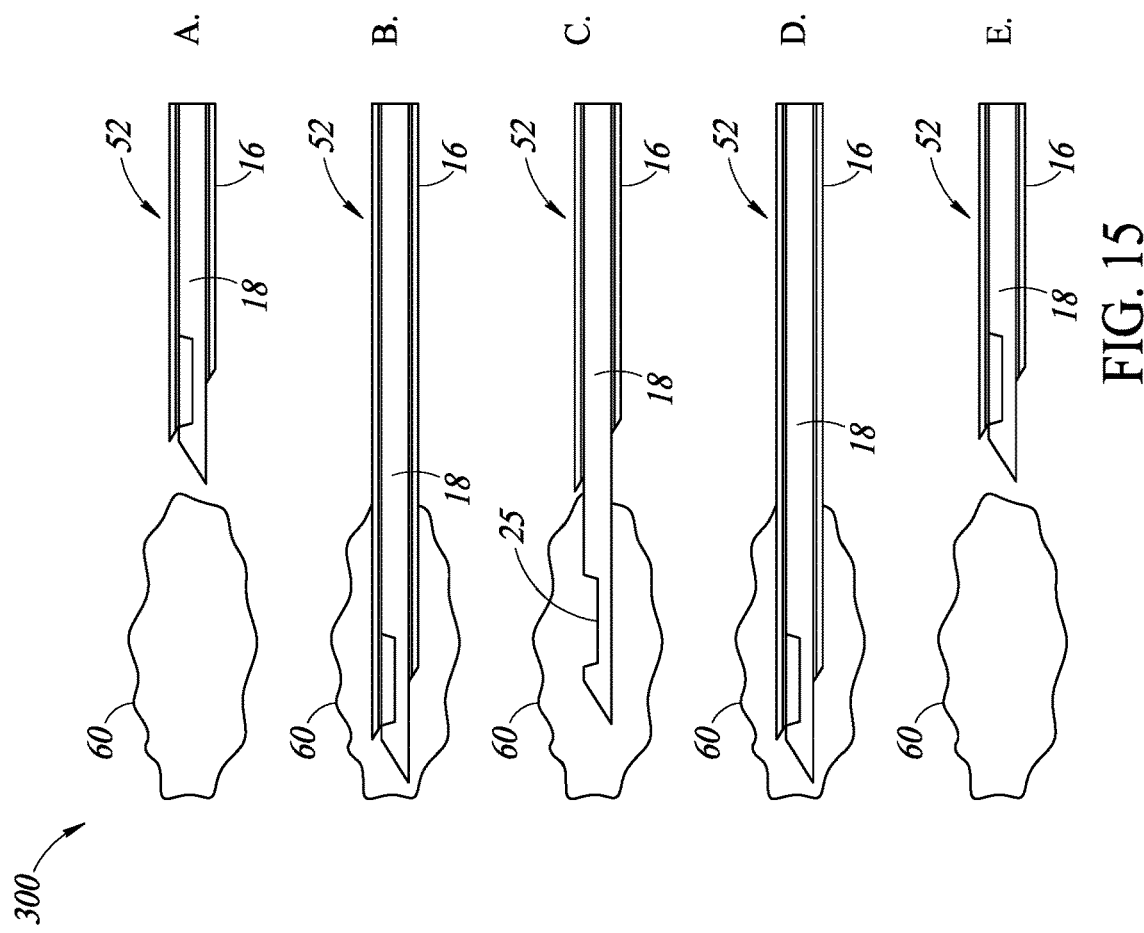
FIGS. 15A-E are schematic representations of a sheathed stylet method of obtaining a biopsy sample.

In sheathed stylet method 300, first stylet 18 and cutting cannula 16 are provided (FIG. 15A). Stylet 18 is positioned within cutting cannula 16 such that notch 25 is covered by cutting cannula 16. Then, stylet 18 and cutting cannula 16 thus combined are advanced into target 60 (FIG. 15B). Once in target 60, cutting cannula 16 is retracted proximally to allow a tissue sample to enter notch 25 (FIG. 15C). Cutting cannula 16 is then fired distally to cut the tissue sample (FIG. 15D). Finally, stylet 18 and cutting cannula 16 are retracted together and the sample is removed (FIG. 15E). While sheathed stylet method 300 has an additional step as compared to exposed stylet method 200, sheathed stylet method 300 may be beneficial in that it reduces the risk of stylet 18 bending—particularly in an area of notch 25 where the area moment of inertia (the physical property that resists bending) and the resistance to bending are substantially less. The use of super-elastic material for curved core biopsy needle 52 increases the possibility of stylet 18 bending at its notch 25 as compared to a standard core biopsy needle. Thus, to prevent instability of core biopsy needle 52 when it is inserted into relatively hard tissue and potential failure of the procedure, sheathed stylet method 300 may be used, since the area moment of inertia is much higher using the combined stylet 18 plus cutting cannula 16 rather than stylet 18 alone. The invention is not limited to the use of sheathed stylet method 300, and in some instances, exposed stylet method 200 or other methods may be used.

Figure 16A:
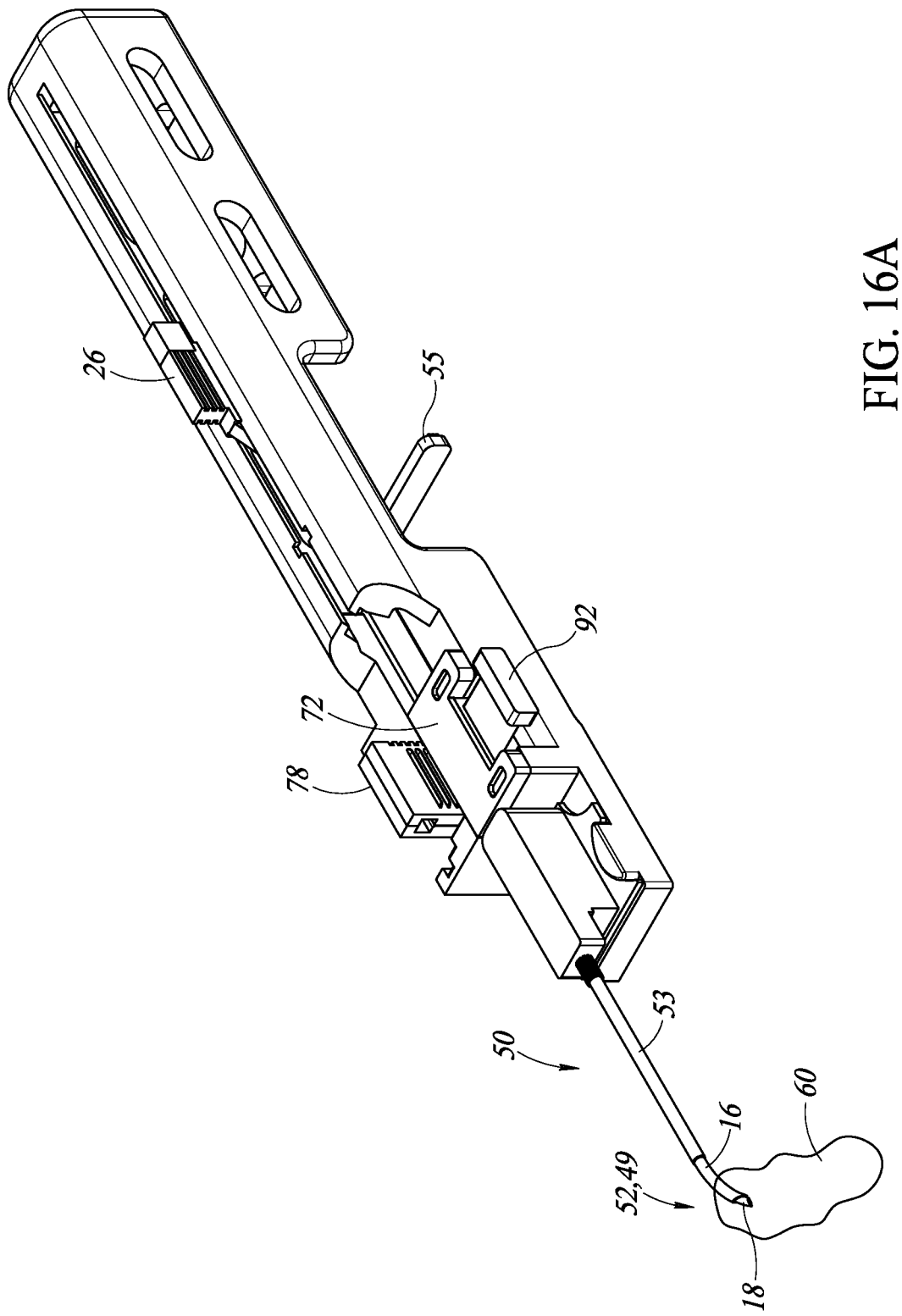
FIGS. 16A-16F are illustrations of the steps of a method of obtaining a biopsy sample, in accordance with embodiments of the present invention.

Reference is now made to FIGS. 16A-16F, which are illustrations of methods of obtaining biopsy samples, in accordance with embodiments of the present invention. Core biopsy needle device 50 is initially positioned such that it is ready to acquire the first tissue sample from a target 60. As shown in FIG. 16A, when core biopsy needle device 50 is adjacent target 60, core biopsy needle 52—including both stylet 18 and cutting cannula 16—is advanced distally past coaxial needle guide 53 and assumes a curved core biopsy needle 49 configuration. In the current embodiment stylet 18 is moved by controller 26 and cutting cannula 16 is moved by trigger handle 55. It is beneficial to advance stylet 18 along with cutting cannula 16 so as to prevent buckling or failure of stylet 18 due to the curved configuration. The user is guided towards target 60 by tracking system 100 (not shown). In embodiments of the invention, parameters including degree of rotation and length of distal advancement needed to reach target 60 may be pre-set. When physiological sensor 107 is integrated into the needle, its signal can verify that the needle tip is in the target (e.g. pH meter indicates entry into a tumor that has higher level of acidity compared with the normal tissue surrounding it).

Figure 16B:
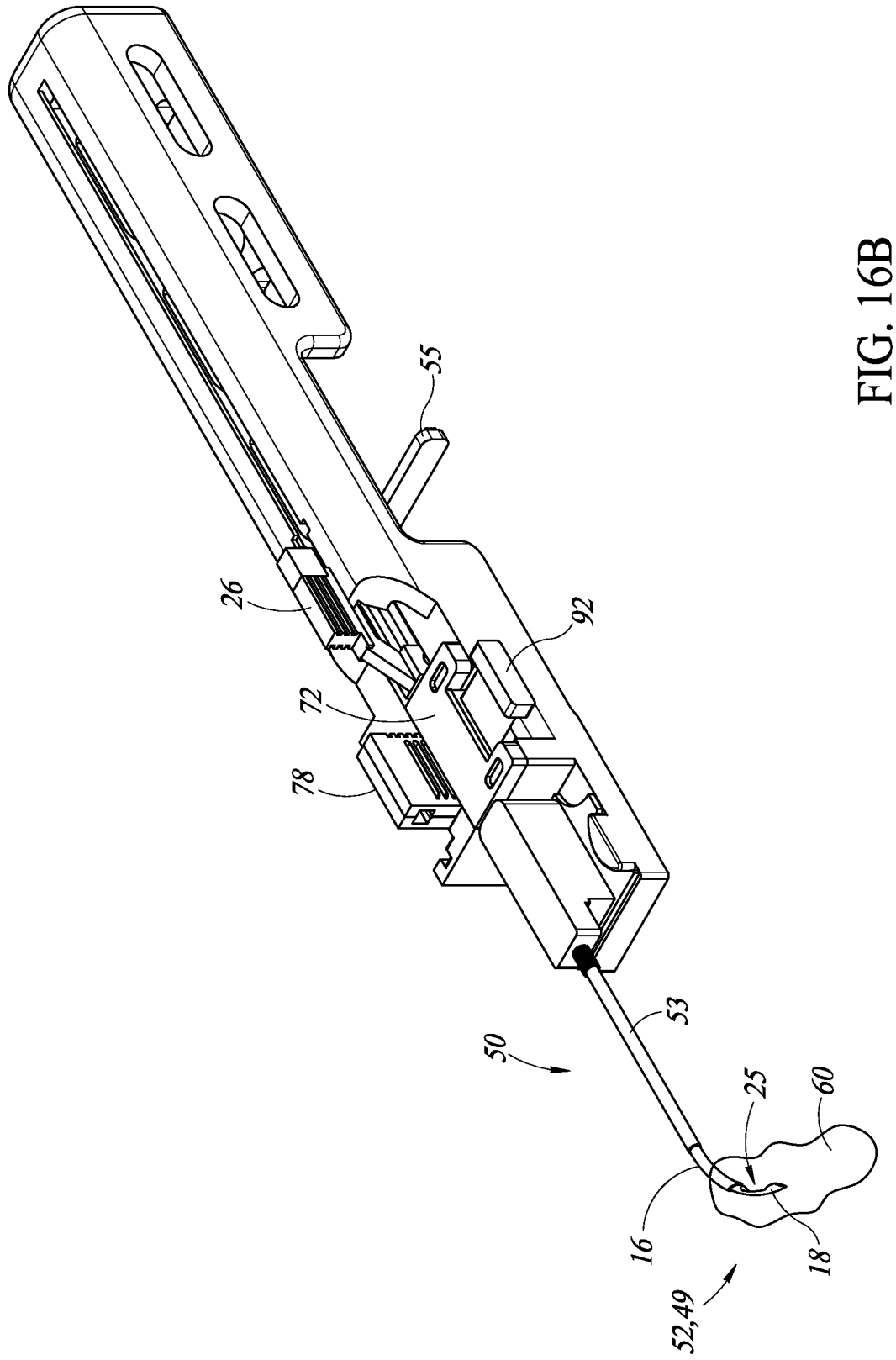

As shown in FIG. 16B, once curved core biopsy needle 52, 49 is in place in target 60, stylet 18 is advanced forward distally past cutting cannula 16 to expose notch 25 such that a first tissue sample from the target 60 fills notch 25 (this is when the exposed stylet method 300 of FIGS. 15A-E is used). As shown in FIG. 16B, notch 25 is exposed since stylet 18 is in a distal position relative to cutting cannula 16. This can also be seen by the position of stylet controller 26, in a forward (i.e. distal) position, compared with FIG. 16A. Trigger handle 55 is in a first position and is holding the spring mechanism in a loaded state and is ready for triggering of cutting cannula 16. As shown in FIGS. 16A and 16B, sample extractor 92 is extended from housing 72, which is a pre-sample extraction position.

Figure 16C:
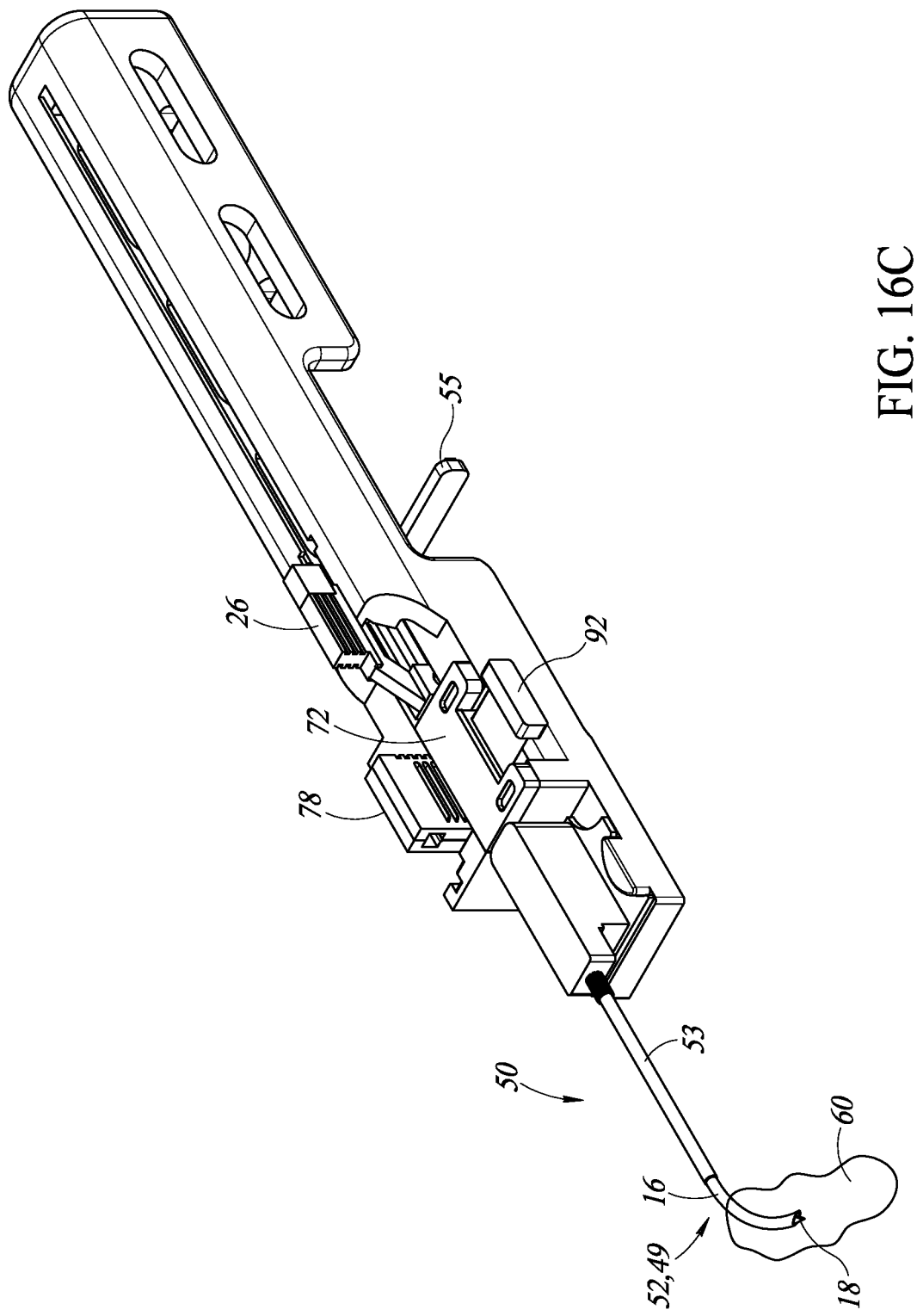

Reference is now made to FIG. 16C, which is an illustration of a continuation of the method of obtaining biopsy samples, in accordance with embodiments of the present invention. As shown in FIG. 16C, cutting cannula 16 is rapidly pushed forward (distally) by activating trigger handle 55 and cuts the tissue sample from the target 60. Now the tissue sample is contained within notch 25 and is enveloped by cutting cannula 16. Trigger handle 55 is in the most forward position after trigger firing, which is distal to the pre-firing position shown in FIG. 16B. Stylet 18 and sample extractor 92 are still in the same position as in FIG. 16B.

Figure 16D:
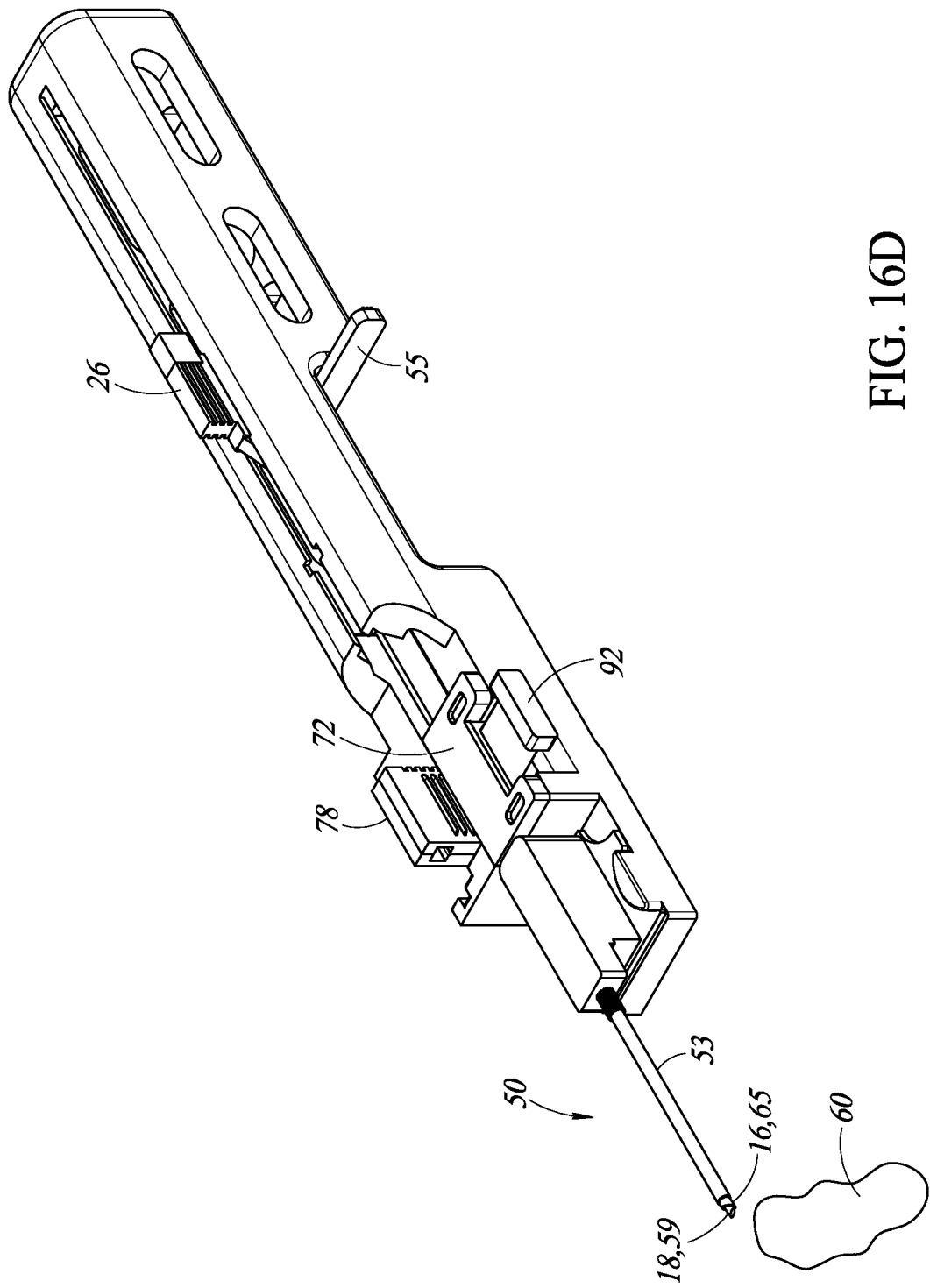

Next, as shown in FIG. 16D, stylet 18 and cutting cannula 16 are pulled back proximally into coaxial needle guide 53 and out of target 60. Now both stylet 18 and cutting cannula 16 assume their straight configurations (59 and 65) since they are both positioned within coaxial needle guide 53. Proximal movement of stylet 18 and cutting cannula 16 can be seen in FIG. 16 by proximal positions of stylet controller 26 and trigger handle 55.

Figure 16E:
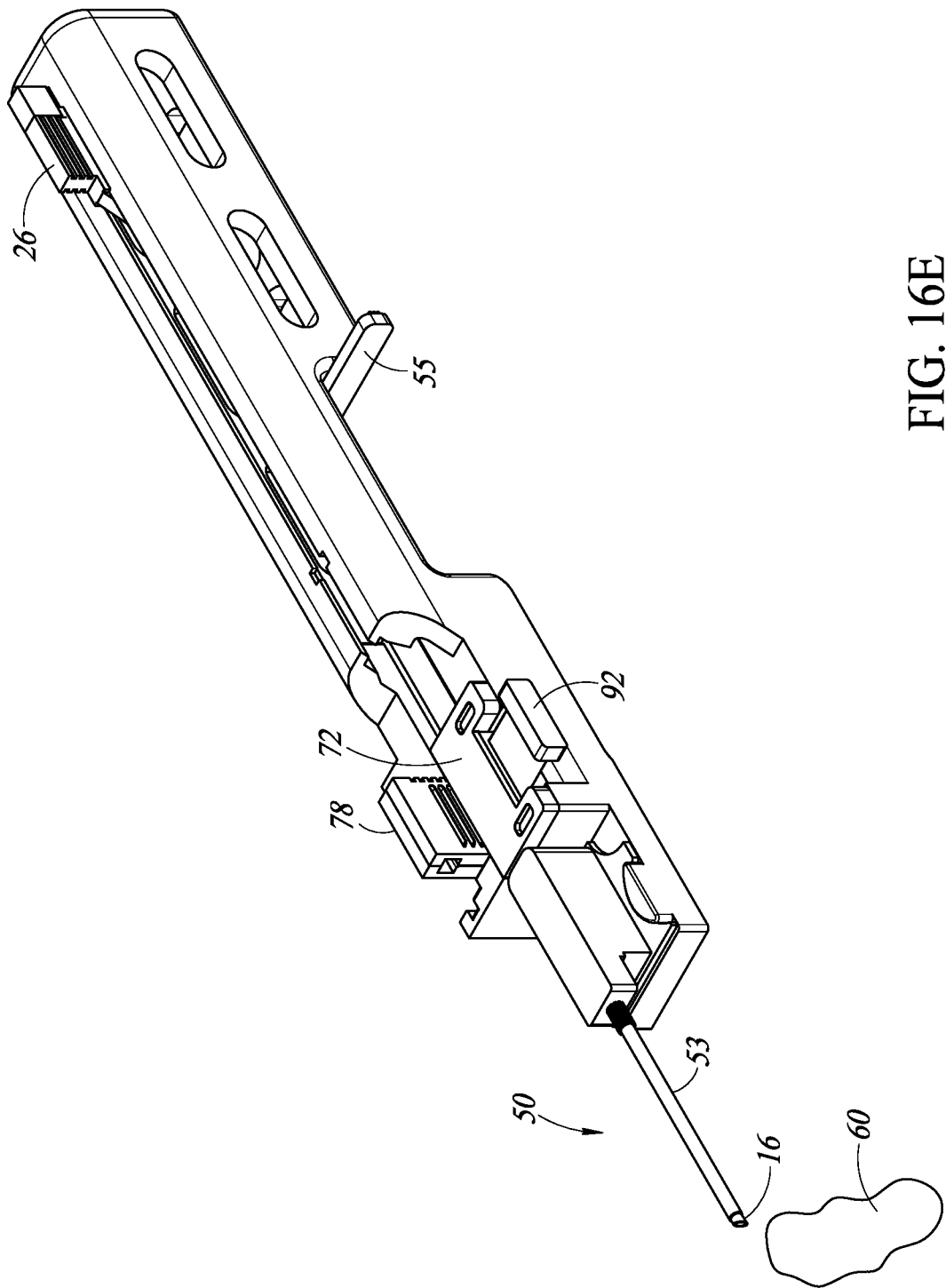

Next, as shown in FIG. 16E, stylet 18 with the tissue sample in its notch 25 is pulled in a proximal direction through the cannula 16, while cannula 16 remains in position. Stylet 18 is pulled back proximally to a point where notch 25 with the tissue sample therein is positioned adjacent to sample cartridge 78. In one embodiment, positioning of notch 25 adjacent to sample cartridge 78 is accomplished by pulling stylet 18 into its most proximal position, which by design aligns notch at the precise location. This can be seen in FIG. 16E with stylet controller 26 at a most proximal position. In other embodiments, a stopping mechanism may be built in to ensure proper alignment. In a motorized embodiment, an optical encoder may be used to monitor the position of the stylet and enable precise positioning by using a microcontroller to control the motions. In any case, notch 25 is aligned with cartridge 78 and sample extractor 92.

Figure 16F:
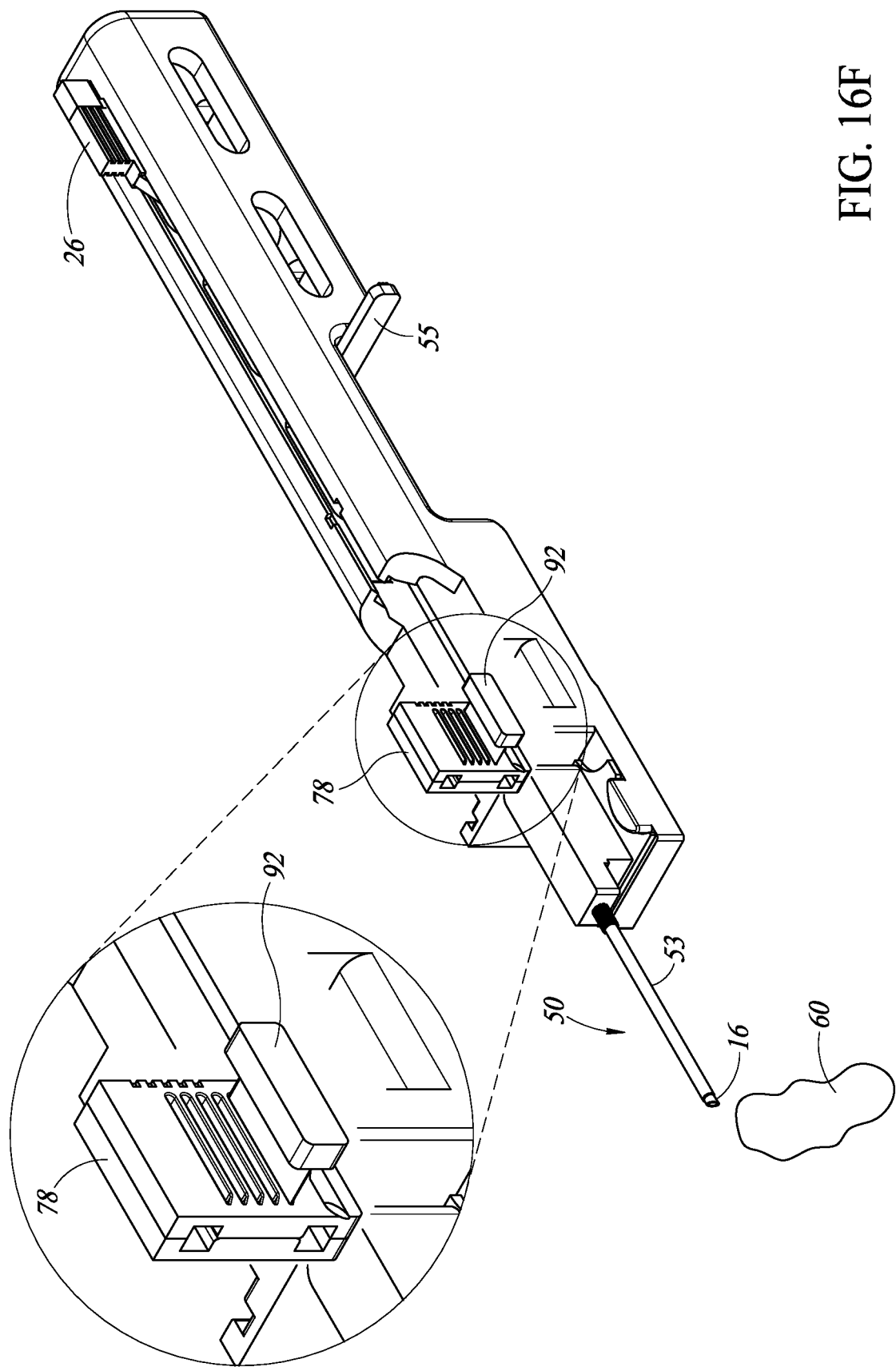

Reference is now made to FIG. 16F, which shows unloading of the sample into cartridge 78. Sample extractor 92 is configured to push the sample into cartridge 78. After the sample has been removed from the stylet 18 and inserted into the cartridge 78, and the sample extractor 92 has been pulled back to its base position, the stylet 18 can be pushed forward through cutting cannula 16 again to prepare for acquiring another sample. Cartridge 78 is configured to accept another sample. This can be done, for example, by manual or automatic advancing of sample cartridge 78 to the next available slot.

The steps shown in FIGS. 16A-16F may be repeated multiple times until all tissue samples are obtained. Before each time the sequence of steps is repeated, the location within target 60 may be changed, by rotating core biopsy needle 52, 49, and/or by adjusting planned forward movement of core biopsy needle 52, 49.

In some embodiments of the invention, a motorized version of biopsy system 10 may be used. A motorized version enables fast acquisition of multiple core tissue samples by automating the needle insertion path through rotation and forward-backward motion of the needle guide. In a motorized device, the operator inserts core biopsy needle 52 to the target and starts an automatic sequence of operations to cut one core tissue sample. Once the sequence is completed, an indicator informs the user that the device is ready to cut the next sample. A motorized device could simplify multi-core acquisition while maintaining the advanced preservation capabilities of the manual device.

The motorized device can be integrated with a mechano-electrical module to perform the required sequence of operations listed above. The module includes a set of miniature motors that move the stylet, load the cannula spring, unload the sample and step the cartridge; a set of micro-switches to monitor its operation; and a microcontroller to control the sequence of operations. The design of the manual device may be adapted into an add-on, single use module that can fast-connect to a re-usable mechano-electrical module. All components that are in contact with the body—including core biopsy needle 52, the cartridge 78 and the biopsy sample unloading apparatus may be suitable for contact with biological substances (skin, tissues, blood).

While certain features of the invention have been illustrated and described herein, many modifications, substitutions, changes, and equivalents may occur to those of ordinary skill in the art. Some additional design optimizations, either in the manual or in the automated version, include the integration of two or more device operation steps, that are currently done separately, into a single step. Some examples include linking the proximal pull-back of the stylet 18, which is a step needed to bring the tissue sample to the cartridge area, to the forward firing of cutting cannula 16. Another example is to link the move of the stylet 18, either proximally or distally, to advancing cartridge 78 to its next slot to receive the next tissue sample.

Additional features may include the ability to preset the length of forward push of the needle, which determines how far (in radial direction) from the needle shaft the tissue core will be acquired.

Additional features include rapid preservation by various preservation methods. For example, fast freezing offers essentially better short-term preservation of the in-vivo genomic and proteomic profiles and can thus improve biomarker research, while preservation with formalin ensures high-quality tissue for histological analysis. The device of the present invention enables standardization of the biopsy procedure and can reduce pre-analytic variability that hampers clinical studies of new targeted drugs.

It is, therefore, to be understood that the appended claims are intended to cover all such modifications and changes as fall within the true spirit of the invention.

What is claimed is:

1. A core biopsy needle device, the core biopsy needle device comprising:
a core biopsy needle having a core biopsy needle proximal end and a core biopsy needle distal end, the core biopsy needle comprising
a stylet having a stylet proximal end and a stylet distal end and a curvable elongate member extending from said stylet proximal end to said stylet distal end along a longitudinal axis, at least one sample receiving portion at said stylet distal end, and a stylet controller at said stylet proximal end, said stylet distal end having a stylet curved configuration and a stylet straight configuration, wherein in said stylet curved configuration, said stylet distal end is curved, wherein in said stylet straight configuration, said stylet distal end is substantially straight, and
a cutting cannula comprised of an outer curvable elongate member coaxially arranged around said stylet, said outer curvable elongate member extending from a cannula proximal end to a cannula distal end, a sample cutting portion at said cannula distal end, wherein said cutting cannula is slidingly movable with respect to said stylet, wherein said stylet is configured to be positioned proximally with respect to said cutting cannula using said stylet controller, said cutting cannula distal end having a cutting cannula curved configuration and a cutting cannula straight configuration, wherein in said cutting cannula curved configuration, said cutting cannula distal end is curved, wherein in said cutting cannula straight configuration, said cutting cannula distal end is substantially straight; and
a coaxial needle guide arranged coaxially around and slidable with respect to said stylet and said cutting cannula, wherein when said stylet distal end is positioned within the coaxial needle guide, said stylet is configured in the stylet straight configuration and when said stylet distal end is positioned distal to the coaxial needle guide, said stylet is configured in the stylet curved configuration and when said cutting cannula distal end is positioned within the coaxial needle guide, said cutting cannula is configured in the cutting cannula straight configuration and when said cutting cannula distal end is positioned distal to the coaxial needle guide, said cutting cannula is configured in the cutting cannula curved configuration, wherein said coaxial needle guide is configured to be positioned within a body tissue, and wherein said core biopsy needle is configured to rotate with respect to the coaxial needle guide and to be deployed distally past the coaxial needle guide to a variety of distances such that a combined use of said positioning of the coaxial needle guide in the body tissue, and said rotation and distal deployment of the core biopsy needle with respect to the coaxial needle guide provides for collection of multiple tissue samples from multiple locations around the longitudinal axis while the coaxial needle guide is in the position within the body tissue, wherein each of the multiple locations is determined by a degree of curvature of the stylet in the stylet curved configuration and by the distal deployment distance of the core biopsy needle.

2. The core biopsy needle device of claim 1, wherein said stylet curved configuration has a stylet curved portion, said stylet curved portion comprising at least said stylet distal end, said stylet curved portion having a constant radius of curvature.

3. The core biopsy needle device of claim 1, wherein said cutting cannula curved configuration has a cannula curved portion, said cannula curved portion comprising at least said cannula distal end, said cannula curved portion having a constant radius of curvature.

4. The core biopsy needle device of claim 1, wherein said coaxial needle guide has a pre-curved configuration in an opposite curve direction from said cutting cannula curved configuration, such that when said cutting cannula distal end is positioned within the coaxial needle guide, the pre-curved configuration of the coaxial needle guide becomes straight.

5. The core biopsy needle device of claim 4, wherein said coaxial needle guide pre-shaped configuration is at a distal portion of said coaxial needle guide.

6. The core biopsy needle device of claim 1, further comprising a motorized control mechanism for controlling movement of said stylet and said cutting cannula.

7. The core biopsy needle device of claim 6, wherein said motorized control mechanism is configured for controlling the rotation and the distal deployment distance of the core biopsy needle with respect to the coaxial needle guide.

8. The core biopsy needle device of claim 6, wherein said motorized control mechanism is configured for controlling the position of the coaxial needle guide within the body tissue.

9. The core biopsy needle device of claim 6, wherein said motorized control mechanism is configured for controlling the collection of tissue samples from multiple locations.

10. The core biopsy needle device of claim 6, wherein the core biopsy needle device is positioned within and is slidingly movable with respect to a biopsy sample collection device along the longitudinal axis, and wherein said motorized control mechanism is configured for controlling the unloading of the tissue samples from the stylet into the biopsy sample collection device.

11. The core biopsy needle device of claim 1, wherein at least one of the multiple locations is at a distance of 10 mm or more from the longitudinal axis.

* * * * *